US011181519B2

(12) United States Patent
Haick et al.

(10) Patent No.: US 11,181,519 B2
(45) Date of Patent: Nov. 23, 2021

(54) SYSTEM AND METHOD FOR DIFFERENTIAL DIAGNOSIS OF DISEASES

(71) Applicant: TECHNION RESEARCH & DEVELOPMENT FOUNDATION LIMITED, Haifa (IL)

(72) Inventors: Hossam Haick, Haifa (IL); Morad Nakhleh, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 396 days.

(21) Appl. No.: 16/308,634

(22) PCT Filed: Jun. 14, 2017

(86) PCT No.: PCT/IL2017/050658
§ 371 (c)(1),
(2) Date: Dec. 10, 2018

(87) PCT Pub. No.: WO2017/216794
PCT Pub. Date: Dec. 21, 2017

(65) Prior Publication Data
US 2019/0271685 A1 Sep. 5, 2019

Related U.S. Application Data

(60) Provisional application No. 62/350,773, filed on Jun. 16, 2016.

(51) Int. Cl.
*A61B 5/08* (2006.01)
*G01N 33/497* (2006.01)

(52) U.S. Cl.
CPC .............. *G01N 33/497* (2013.01); *A61B 5/08* (2013.01); *A61B 5/082* (2013.01);
(Continued)

(58) Field of Classification Search
CPC ......... G01N 33/497; G01N 2033/4975; G01N 2800/12; G01N 2800/28; G01N 2800/347;
(Continued)

(56) References Cited

U.S. PATENT DOCUMENTS 5,996,586 A 12/1999 Phillips
6,312,390 B1 11/2001 Phillips
(Continued)

FOREIGN PATENT DOCUMENTS

CN 103018282 A 4/2013
CN 104583762 A 4/2015
(Continued)

OTHER PUBLICATIONS

Feng, Xinliang, et al. "Synthesis, helical organization, and fibrous formation of C 3 symmetric methoxy-substituted discotic hexa-peri-hexabenzocoronene." Chemistry of Materials 20.9 (2008): 2872-2874 (Year: 2008).*
(Continued)

*Primary Examiner* — Andrey Shostak
(74) *Attorney, Agent, or Firm* — Roach, Brown, Mccarthy & Gruber, P.C.; Kevin D. McCarthy

(57) ABSTRACT

The present invention provides a system and method for diagnosing, screening or monitoring a disease by analyzing the breath of a test subject using a selected definitive sensor set in conjunction with a pattern recognition analyzer, wherein the pattern recognition analyzer receives output signals of the sensor set, compares them to disease-specific patterns derived from a database of response patterns of the sensor set to exhaled breath of subjects with known diseases, wherein each of the disease-specific patterns is characteristic of a particular disease, and selects a closest match between the output signals of the sensor set and the disease-specific
(Continued)

pattern. The present invention further provides a method of diagnosing, screening or monitoring a disease based on the determination of levels of volatile organic compounds (VOCs) from a universal biomarker set, including 2-ethylhexanol, 3-methylhexane, 5-ethyl-3-methyl-octane, acetone, ethanol, ethyl acetate, ethylbenzene, isononane, isoprene, nonanal, styrene, toluene and undecane.

19 Claims, 8 Drawing Sheets

(52) U.S. Cl.
CPC . *G01N 2033/4975* (2013.01); *G01N 2800/12* (2013.01); *G01N 2800/28* (2013.01); *G01N 2800/347* (2013.01)

(58) Field of Classification Search
CPC .......... G16H 50/20; A61B 5/08; A61B 5/082; A61B 2562/0285; A61B 5/7264
See application file for complete search history.

(56) References Cited

U.S. PATENT DOCUMENTS

| | | |
|---|---|---|
| 6,540,691 B1 | 4/2003 | Phillips |
| 6,609,068 B2 | 8/2003 | Cranley |
| 6,620,109 B2 | 9/2003 | Hanson |
| 6,773,926 B1 | 8/2004 | Freund |
| 6,841,391 B2 | 1/2005 | Lewis |
| 7,076,371 B2 | 7/2006 | Fu |
| 7,153,272 B2 | 12/2006 | Talton |
| 8,366,630 B2 | 2/2013 | Haick |
| 8,481,324 B2 | 7/2013 | Haick |
| 8,597,953 B2 | 12/2013 | Haick |
| 8,945,935 B2 | 2/2015 | Haick |
| 8,999,244 B2 | 4/2015 | Haick |
| 9,359,197 B2 | 6/2016 | Haick |
| 9,678,059 B2 | 6/2017 | Haick |
| 2002/0081745 A1 | 6/2002 | Ross |
| 2004/0006257 A1 | 1/2004 | Burch |
| 2004/0127808 A1 | 7/2004 | Vaughan |
| 2005/0287552 A1 | 12/2005 | Lin |
| 2006/0034731 A1 | 2/2006 | Lewis |
| 2007/0048180 A1 | 3/2007 | Gabriel |
| 2007/0062255 A1 | 3/2007 | Talton |
| 2010/0188110 A1 | 7/2010 | Sun |
| 2010/0273665 A1 | 10/2010 | Haick |
| 2011/0098591 A1 | 4/2011 | Haick |
| 2011/0244584 A1 | 10/2011 | Haick |
| 2011/0269632 A1 | 11/2011 | Haick |
| 2011/0277538 A1* | 11/2011 | Haick ................. B82Y 15/00 73/23.3 |
| 2012/0245434 A1 | 9/2012 | Haick |
| 2012/0245854 A1* | 9/2012 | Haick ................. B82Y 15/00 702/19 |
| 2012/0326092 A1 | 12/2012 | Haick |
| 2013/0034910 A1 | 2/2013 | Haick |
| 2013/0059758 A1 | 3/2013 | Haick |
| 2013/0143247 A1* | 6/2013 | Haick ............. G01N 33/57423 435/15 |
| 2013/0150261 A1* | 6/2013 | Haick ................. G01N 33/497 506/12 |
| 2013/0236981 A1 | 9/2013 | Haick |
| 2015/0301021 A1 | 10/2015 | Haick |
| 2016/0077069 A1 | 3/2016 | Kim |
| 2017/0347936 A1* | 12/2017 | Stahmann ............ A61B 5/7282 |

FOREIGN PATENT DOCUMENTS

| | | |
|---|---|---|
| WO | 0061002 A1 | 10/2000 |
| WO | 2010079490 A1 | 7/2010 |
| WO | 2010079491 A1 | 7/2010 |
| WO | 2011083473 A1 | 7/2011 |
| WO | 2011148371 A1 | 12/2011 |
| WO | 2012023138 A2 | 2/2012 |

OTHER PUBLICATIONS

Nakhleh, Morad K., Yoav Y. Broza, and Hossam Haick. "Monolayer-capped gold nanoparticles for disease detection from breath." Nanomedicine 9.13 (2014): 1991-2002 (Year: 2014).*
Broza, Yoav Y., and Hossam Haick. "Nanomaterial-based sensors for detection of disease by volatile organic compounds." Nanomedicine 8.5 (2013): 785-806 (Year: 2013).*
Miekisch et al., (2004) Diagnostic potential of breath analysis-focus on volatile organic compounds. Clin Chim Acta 347(1-2): 25-39.
Moorhead et al., (2011) Modelling acute renal failure using blood and breath biomarkers in rats. Comput. Methods Programs Biomed 101(2): 173-182.
Nakhleh et al., (2014) Detecting active pulmonary tuberculosis with a breath test using nanomaterial-based sensors. Eur Respir J 43(5): 1522-1525.
Nakhleh et al., (2014) Monolayer-capped gold nanoparticles for disease detection from breath. Nanomedicine (Lond) 9(13): 1991-2002.
Nakhleh et al., (2015) Distinguishing idiopathic Parkinson's disease from other parkinsonian syndromes by breath test. Parkinsonism Relat Disord 21(2): 150-153.
Nakhleh et al., (2016) Artificially Intelligent Nanoarray for the Detection of Preeclampsia under Real-World Clinical Conditions. Adv Healthcare Mater 1(9): 1600132; 6 pages.
Nakhleh et al., (2017) Diagnosis and Classification of 17 Diseases from 1404 Subjects via Pattern Analysis of Exhaled Molecules. ACS Nano 11(1): 112-125 with Supporting Information.
Nardi-Agmon et al., (2016) Exhaled Breath Analysis for Monitoring Response to Treatment in Advanced Lung Cancer. J Thorac Oncol 11(6): 827-837.
Ouyang and Pawliszyn (2006) SPME in environmental analysis. Anal Bioanal Chem 386(4): 1059-1073.
Peled et al., (2012) Non-invasive breath analysis of pulmonary nodules. J Thorac Oncol 7(10): 1528-1533.
Peled et al., (2013) Volatile fingerprints of cancer specific genetic mutations. Nanomedicine 9(6): 758-766.
Peng et al., (2008) Detecting simulated patterns of lung cancer biomarkers by random network of single walled carbon nanotubes coated with nanopolymeric organic materials. Nano Lett 8(11): 3631-3635.
Peng et al., (2009) Diagnosing lung cancer in exhaled breath using gold nanoparticles. Nat Nanotechnol 4(10) 669-673.
Peng et al., (2010) Detection of lung, breast, colorectal, and prostate cancers from exhaled breath using a single array of nanosensors. Br J Cancer 103(4): 542-551.
Pennazza et al., (2011) Monitoring of melanoma released volatile compounds by a gas sensors array: From in vitro to in vivo experiments. Sensors and Actuators B: Chemical 154(2): 288-294.
Phillips (2003) Volatile markers of breast cancer in the breath. Breast J 9(3): 184-191.
Phillips et al., (1999) Volatile organic compounds in breath as markers of lung cancer: a cross-sectional study. Lancet 353(9168): 1930-1933.
Phillips et al., (2003) Detection of lung cancer with volatile markers in the breath. Chest 123(6): 2115-2123.
Phillips et al., (2006) Prediction of breast cancer using volatile biomarkers in the breath. Breast Cancer Res Treat 99(1): 19-21.
Phillips et al., (2007) Prediction of lung cancer using volatile biomarkers in breath. Cancer Biomark 3(2): 95-109.
Phillips et al., (2010) Volatile biomarkers in the breath of women with breast cancer. J Breath Res 4(2): 026003 (8 pages).
Poli et al., (2005) Exhaled volatile compounds in patients with non-small cell lung cancer: cross sectional and nested short-term follow-up study. Respiratory Research 6: 71-81.
Poli et al., (2008) Breath analysis in non small cell lung cancer patients after surgical tumour resection. Acta Biomed 79(Suppl 1): 64-72.

(56) References Cited

OTHER PUBLICATIONS

Polman et al., (2005) Diagnostic criteria for multiple sclerosis: 2005 revisions to the "McDonald Criteria". Ann Neurol 58(6): 840-846.
Rock et al., (2008) Electronic nose: current status and future trends. Chem Rev 108(2): 705-725.
Schmutzhard et al., (2008) Pilot study: volatile organic compounds as a diagnostic marker for head and neck tumors. Head Neck 30(6): 743-749.
Shao et al., (2011) Recent patents on nanosensor for tumor biomarker detection. Nano Biomedicine & Engineering 3(1): 66-72.
Shehada et al., (2015) Ultrasensitive silicon nanowire for real-world gas sensing: noninvasive diagnosis of cancer from breath volatolome. Nano Lett 15(2): 1288-1295.
Shehada et al., (2016) Silicon Nanowire Sensors Enable Diagnosis of Patients via Exhaled Breath. ACS Nano 10(7): 7047-7057.
Shuster et al., (2011) Classification of breast cancer precursors through exhaled breath. Breast Cancer Res Treat 126(3): 791-796.
Simonneau et al., (2009) Updated clinical classification of pulmonary hypertension. J Am Coll Cardiol 54(1 Suppl): S43-S54.
Sitbon et al., (2005) Long-term response to calcium channel blockers in idiopathic pulmonary arterial hypertension. Circulation 111(23): 3105-3111.
Smith et al., (2011) Can volatile compounds in exhaled breath be used to monitor control in diabetes mellitus? J Breath Res 5(2): 022001; 9 pages.
Song et al., (2009) Quantitative breath analysis of volatile organic compounds of lung cancer patients. Lung Cancer 67(2): 227-231.
Stetter et al., (2000) New sensor arrays and sampling systems for a modular electronic nose. Sensors and Actuators B: Chemical 69(3): 410-419.
Sztrymf et al., (2008) Clinical outcomes of pulmonary arterial hypertension in carriers of BMPR2 mutation. Am J Respir Crit Care Med 177(12): 1377-1383.
Tisch and Haick (2010) Nanomaterials for cross-reactive sensor arrays. MRS Bulletin 35(10): 797-803.
Tisch and Haick (2011) Arrays of chemisensitive monolayer-capped metallic nanoparticles for diagnostic breath testing. Rev Chem Eng 26: 171-179.
Turner (2011) Potential of breath and skin analysis for monitoring blood glucose concentration in diabetes. Expert Rev Mol Diagn 11(5): 497-503.
Vishinkin and Haick (2015) Nanoscale Sensor Technologies for Disease Detection via Volatolomics. Small 11(46): 6142-6164.
Voss et al., (2005) Smelling renal dysfunction via electronic nose. Ann Biomed Eng 33(5): 656-660.
Wang et al., (2014) Artificial sensing intelligence with silicon nanowires for ultraselective detection in the gas phase. Nano Lett 14(2): 933-938.
Wang et al., (2016) A Highly Sensitive Diketopyrrolopyrrole-Based Ambipolar Transistor for Selective Detection and Discrimination of Xylene Isomers. Adv Mater 28(21): 4012-4018.
Xu et al., (2013) A nanomaterial-based breath test for distinguishing gastric cancer from benign gastric conditions. Br J Cancer 108(4): 941-950.
Yu et al., (2003) Detection volatile organic compounds in breath as markers of lung cancer using a novel electronic nose. Sensors, Proceedings of IEEE 2:1333-1337.
Zhang et al., (2002) Vapour sensing using surface functionalized gold nanoparticles. Nanotechnology 13(3): 439-444.
Zhao et al., (1997) Soft lithographic methods for nano-fabrication. J Mater Chem 7:1069-1074.
Zhou et al., (2012) Gold-platinum alloy nanowires as highly sensitive materials for electrochemical detection of hydrogen peroxide. Anal Chim Acta 757: 56-62.
Zilberman et al., (2009) Spongelike Structures of Hexa-peri-hexabenzocoronene Derivatives Enhance the Sensitivity of Chemiresistive Carbon Nanotubes to Nonpolar Volatile Organic Compounds of Cancer. Langmuir 25(9): 5411-5416.
Zilberman et al., (2010) Carbon nanotube/hexa-peri-hexabenzocoronene bilayers for discrimination between nonpolar volatile organic compounds of cancer and humid atmospheres. Adv Mater 22(38): 4317-4320.
Kim ID., Choi SJ., Kim SJ., Jang JS. (2015) Exhaled Breath Sensors. In: Kyung CM. (eds) Smart Sensors for Health and Environment Monitoring. KAIST Research Series. Springer, Dordrecht; pp. 19-49. https://doi.org/10.1007/978-94-017-9981-2_2.
Vishinkin and Haick (2015) Artificially intelligent nanoarrays for disease detection via volatolomics. 2015 IEEE International Electron Devices Meeting (IEDM), Dec. 7-9, 2015; Washington, DC, USA. DOI: 10.1109/IEDM.2015.7409821; 4 pages.
Alkhouri et al., (2015) Isoprene in the Exhaled Breath is a Novel Biomarker for Advanced Fibrosis in Patients with Chronic Liver Disease: A Pilot Study. Clin Transl Gastroenterol 6: e112; 7 pages.
Amal et al., (2012) The scent fingerprint of hepatocarcinoma: in-vitro metastasis prediction with volatile organic compounds (VOCs). Int J Nanomedicine 7: 4135-4146.
Amal et al., (2015) Assessment of ovarian cancer conditions from exhaled breath. Int J Cancer 136(6): E614-E622.
Amal et al., (2016) Breath testing as potential colorectal cancer screening tool. Int J Cancer 138(1): 229-236.
Amal et al., (2016) Detection of precancerous gastric lesions and gastric cancer through exhaled breath. Gut 65(3): 400-407.
Amann et al., (2010) Analysis of exhaled breath for screening of lung cancer patients, memo—Magazine of European Medical Oncology 3(3): 106-112.
Amann et al., (2011) Lung cancer biomarkers in exhaled breath. Expert Rev Mol Diagn 11(2): 207-217.
Amorim and de L Cardeal (2007) Breath air analysis and its use as a biomarker in biological monitoring of occupational and environmental exposure to chemical agents. J Chromatogr B Analyt Technol Biomed Life Sci 853(1-2): 1-9.
Bajtarevic et al., (2009) Noninvasive detection of lung cancer by analysis of exhaled breath. BMC Cancer 29(9): 348 (16 pages).
Barash et al., (2009) Sniffing the Unique "Odor Print" of Non-Small-Cell Lung Cancer with Gold Nanoparticles. Small 5 (22): 2618-2624.
Barash et al., (2012) Classification of lung cancer histology by gold nanoparticle sensors. Nanomedicine 8(5): 580-589.
Barash et al., (2015) Differentiation between genetic mutations of breast cancer by breath volatolomics. Oncotarget 6(42): 44864-44876.
Broza and Haick (2013) Nanomaterial-based sensors for detection of disease by volatile organic compounds. Nanomedicine (Lond) 8(5): 785-806.
Brust et al., (1994) Synthesis of Thiol-derivatised Gold Nanoparticles in a Two-phase Liquid-Liquid System. J Chem Soc Chem Commun 7:801-802.
Chen et al., (2007) A study of the volatile organic compounds exhaled by lung cancer cells in vitro for breath diagnosis. Cancer 110(4): 835-844.
Coate et al., (2009) Molecular predictive and prognostic markers in non-small-cell lung cancer. Lancet Oncol 10(10): 1001-1010.
Cohen-Kaminsky et al., (2013) A proof of concept for the detection and classification of pulmonary arterial hypertension through breath analysis with a sensor array. Am J Respir Crit Care Med 188(6): 756-759.
Davies et al., (2014) Breath analysis of ammonia, volatile organic compounds and deuterated water vapor in chronic kidney disease and during dialysis. Bioanalysis 6(6): 843-857 abstract.
Davies et al., (2014) Unique volatolomic signatures of TP53 and KRAS in lung cells. Br J Cancer 111(6): 1213-1221.
Di Natale et al., (2003) Lung cancer identification by the analysis of breath by means of an array of non-selective gas sensors. Biosens Bioelectron 18(10): 1209-1218.
Dovgolevsky et al., (2009) Chemically Sensitive Resistors Based on Monolayer-Capped Cubic Nanoparticles: Towards Configurable Nanoporous Sensors. Small 5(10): 1158-1161.
Dovgolevsky et al., (2010) Monolayer-capped cubic platinum nanoparticles for sensing nonpolar analytes in highly humid atmospheres. J Phys Chem C 114(33): 14042-14049.

(56) References Cited

OTHER PUBLICATIONS

Dragonieri et al., (2009) An electronic nose in the discrimination of patients with non-small cell lung cancer and COPD. Lung Cancer 64(2): 166-170.
Galiè et al., (2009) Guidelines for the diagnosis and treatment of pulmonary hypertension. Eur Respir J 34(6): 1219-1263.
Gelperin and Johnson (2008) Nanotube-based sensor arrays for clinical breath analysis. J Breath Res 2(3): 037015 (6 pages).
Geng Song et al., (2008) The quantitative detection of the trace amount of the volatile organic compound in the breath of the lung cancer patient in early stage. Journal of Anhui pharmaceutical university 43(3): 323-325. Translated abstract on p. 325.
Gordon et al., (1985) Volatile organic compounds in exhaled air from patients with lung cancer. Clin Chem 31(8): 1278-1282.
Gouma and Kalyanasundaram (2008) A selective nanosensing probe for nitric oxide. Appl Phys Lett 93: 244102; 4 pages.
Gouma and Stanacevic (2011) Selective Nanosensor Array Microsystem For Exhaled Breath Analysis. Procedia Engineering 25:1557-1560.
Gruber et al., (2014) Analysis of exhaled breath for diagnosing head and neck squamous cell carcinoma: a feasibility study. Br J Cancer 111(4): 790-798.
Haick (2007) Chemical Sensors Based Molecularly Modified Metallic Nanoparticles. J Phys D 40: 7173-7186.
Haick et al., (2009) Sniffing chronic renal failure in rat model by an array of random networks of single-walled carbon nanotubes. ACS Nano 3(5): 1258-1266.
Haick et al., (2014) Assessment, origin, and implementation of breath volatile cancer markers. Chem Soc Rev 43(5): 1423-1449.
Hakim et al., (2011) Diagnosis of head-and-neck cancer from exhaled breath. Br J Cancer 104(10): 1649-1655.
Hakim et al., (2012) Volatile organic compounds of lung cancer and possible biochemical pathways. Chem Rev 112(11): 5949-5966.
Hicks et al., (2015) Analysis of Exhaled Breath Volatile Organic Compounds in Inflammatory Bowel Disease: A Pilot Study. J Crohns Colitis 9(9): 731-737.
Homede et al., (2016) Printing Ultrasensitive Artificially Intelligent Sensors Array with a Single Self-Propelled Droplet Containing Nanoparticles. Adv Func Mater 26(35): 6359-6370.
Hostetler et al., (1998) Alkanethiolate Gold Cluster Molecules with Core Diameters from 1.5 to 5.2 nm: Core and Monolayer Properties as a Function of Core Size. Langmuir 14(1):17-30.
Ionescu et al., (2011) Detection of multiple sclerosis from exhaled breath using bilayers of polycyclic aromatic hydrocarbons and single-wall carbon nanotubes. ACS Chem Neurosci 2(12): 687-693.
Karban et al., (2016) Programmed Nanoparticles for Tailoring the Detection of Inflammatory Bowel Diseases and Irritable Bowel Syndrome Disease via Breathprint. Adv Healthc Mater 5(18): 2339-2344.
Konvalina and Haick (2014) Sensors for breath testing: from nanomaterials to comprehensive disease detection. Acc Chem Res 47(1): 66-76.
Kumar et al., (2015) Mass Spectrometric Analysis of Exhaled Breath for the Identification of Volatile Organic Compound Biomarkers in Esophageal and Gastric Adenocarcinoma. Ann Surg 262(6): 981-990.
Li et al., (2014) Investigation of potential breath biomarkers for the early diagnosis of breast cancer using gas chromatography-mass spectrometry. Clin Chim Acta 436: 59-67.
Ligor et al., (2009) Determination of volatile organic compounds in exhaled breath of patients with lung cancer using solid phase microextraction and gas chromatography mass spectrometry. Clin Chem Lab Med 47(5): 550-560.
Lindinger et al., (1998) On-line monitoring of volatile organic compounds at pptv levels by means of proton-transfer-reaction mass spectrometry (PTR-MS) medical applications, food control and environmental research. Int J Mass Spectrom Ion Process 173(3): 191-241.
Lindinger et al., Environmental, Food and Medical Applications of Proton-Transfer-Reaction Mass Spectrometry (PTR-MS). In: Advances in Gas-Phase Ion Chemistry, vol. 4. Edited by Adams NG and Babcock LM. 2001; Elsevier Science B.V., Amsterdam, The Netherlands; pp. 1-48.
Machado et al., (2005) Detection of lung cancer by sensor array analyses of exhaled breath. Am J Respir Crit Care Med 171(11): 1286-1291.
Marom et al., (2012) Gold nanoparticle sensors for detecting chronic kidney disease and disease progression. Manomedicine (Lond) 7(5): 639-50.
Mazzone (2008) Progress in the development of a diagnostic test for lung cancer through the analysis of breath volatiles. J Breath Res 2(3): 037014 (6 pages).
Mazzone et al., (2008) Analysis of volatile organic compounds in the exhaled breath for the diagnosis of lung cancer. J Thorac Oncol 3(7): 774-780.

\* cited by examiner

SYSTEM AND METHOD FOR DIFFERENTIAL DIAGNOSIS OF DISEASES

FIELD OF THE INVENTION

The present invention relates to a system and methods for diagnosing a disease through breath analysis.

BACKGROUND OF THE INVENTION

Since ancient medicine, physicians learned to evaluate their patients, inter alia, by their breath odor. Hippocrates (around 400 B.C.), for instance, told his students: "smell your patients' breath", in order to search for clues of diseases such as diabetes (sweet smell) and kidney failure (smell of urine). In the 1700s, Antoine Lavoisier was the first to prove that humans' exhaled breath contains carbon dioxide as a metabolic byproduct, and, furthermore, that its levels are measurable and informative. In 1971 the Nobel Prize laureate Linus Pauling analyzed for the first time a breath sample using gas-liquid partition chromatography. In his experiments, Pauling revealed that the human exhaled breath contains hundreds of molecular markers that are found in very small concentrations. This family of markers was termed volatile organic compounds (VOCs; organic molecules with low molecular weight, low boiling point and/or high vapor pressure) which may emanate from or as a result of a disease state.

Since the findings of Linus Pauling, thousands of researches have reported significant alterations in the breath composition of various diseases, including various types of cancer, internal diseases, neurodegenerative diseases, infectious diseases and others [Broza, Y. Y. & Haick, H. Nanomedicine (Future Medicine) 8, 785-806 (2013); Nakhleh, M., Broza, Y. Y., Haick, H. & 2014, Nanomedicine (Future Medicine) 9, 1991-2002].

Considering modern criteria in clinical practice, analysis of exhaled breath should be low-cost, low-energy, ultraminiaturized, easily repeated at specific time intervals, and have little or no impact on the day-to-day activity of the person diagnosed. Basically, recognition of VOCs by nanotechnology-based sensors can be achieved by selective detection of (pre)identified VOCs [Vishinkin, R.; Haick, H., Small 2015, 11, 6142-6164; Gouma, P.; Stanacevic, M., Procedia Eng. 2011, 25, 1557-1560; Gouma, P. I.; Kalyanasundaram, K., Appl. Phys. Lett. 2008, 93, 244102; Zhou, Y.; Yu, G.; Chang, F.; Hu, B.; Zhong, C. J. Anal. Chim. Acta 2012, 757, 56-62]. This approach is useful to detect specific well-defined VOCs in the presence of interfering gaseous species or background using a highly selective receptor designed for this purpose, which is a laborious business. Despite advances in detection of VOCs by highly selective nanomaterial-based recognition methods, this has only been possible to date for indicating VOCs from a relatively narrow spectrum of diseases. While specific recognition in controlled backgrounds and interferences is achievable, currently most diseases cannot be identified properly by individual VOCs alone [Haick, H.; Broza, Y. Y.; Mochalski, P.; Ruzsanyi, V.; Amann, A., Chem. Soc. Rev. 2014, 43, 1423-1449, Konvalina, G.; Haick, H., Acc. Chem. Res. 2014, 47, 66-76]. An additional limitation is the problem of synthesizing highly selective nanomaterials for each VOC, notably when they are nonpolar.

A complementary approach for disease detection and classification of a wider variety of diseases relies on cross-reactive (i.e., semiselective) nanotechnology-based sensor arrays, using pattern recognition, also termed herein an "artificially intelligent nanoarray" [Shehada, N. et al., ACS Nano 2016, 10, 7047-7057; Wang, B.; Cancilla, J. C.; Torrecilla, J. S.; Haick, H. Nano Lett. 2014, 14, 933-938; Nakhleh, M. K.; Baram, S.; Jeries, R.; Salim, R.; Haick, H.; Hakim, M., Adv. Healthcare Mater. 2016, 1600132; Homede, E.; Abo Jabal, M.; Ionescu, R.; Haick, H., Adv. Funct. Mater. 2016, 26, 6359-6370]. In contrast to the selective method, an artificially intelligent nanoarray is more suitable for rapid diagnostic methods in which evaluation of a VOC compendium is qualitative and semiquantitative, with selectivity being achieved through pattern recognition of the compendium. Due to cross-reactivity, each sensor responds to a variety of VOCs, thereby allowing sensing and analysis of individual components from multicomponent samples [Peng, G.; Tisch, U.; Adams, O.; Hakim, M.; Shehada, N.; Broza, Y. Y.; Billan, S.; Abdah-Bortnyak, R.; Kuten, A.; Haick, H., Nat. Nanotechnol. 2009, 4, 669-673; Shehada, N.; Brönstrup, G.; Funka, K.; Christiansen, S.; Leja, M.; Haick, H., Nano Lett. 2015, 15, 1288-1295; Wang, B. et al., Adv. Mater. 2016, 28, 4012-4018]. The concept of the artificially intelligent nanoarray is based on the ability of each sensor to detect all or part of the sample compounds. Although these sensors may have a sensitivity to a specific analyte (or VOC) lower than that of a selective sensor, they are more versatile in detecting multicomponent and complex VOC mixtures in different atmospheres. Artificially intelligent nanoarrays of different composition were assessed in a series of separate laboratory (preclinical) and clinical studies for the detection of a wide range of cancerous and noncancerous diseases [Hakim, M. et al., Chem. Rev. 2012, 112, 5949-5966; Cohen-Kaminsky, S. et al., Am. J. Respir. Crit. Care Med. 2013, 188, 756-759; Amal, H. et al., Int. J. Cancer 2016, 138, 229-236; Amal, H. et at, Gut 2016, 65, 400-407; Amal, H. et al., Int. J. Cancer 2015, 136, E614-E622; Barash, O. et al., Nanomedicine (N. Y., NY, U. S.) 2012, 8, 580-589; Barash, O.; et al., Oncotarget 2015, 6, 44864-44876; Davies, M. P. et al., Br. J. Cancer 2014, 111, 1213-1221; Hakim, M. et al., Br. J. Cancer 2011, 104, 1649-1655; Peled, N. et al., J. Thorac. Oncol. 2012, 7, 1528-1533; Peng, G. et al., Br. J. Cancer 2010, 103, 542-551; Ionescu, R. et at, Neurosci. 2011, 2, 687-693; (50) Karban, A. et al., Adv. Healthcare Mater. 2016, 5, 2339-2344; Marom, O. et al., Nanomedicine (London, U. K.) 2012, 7, 639-650; Nakhleh, M. K. et al., Parkinsonism Relat. Disord. 2015, 21, 150-153; Nakhleh, M. K. et at, Eur. Respir. J. 2014, 43, 1522-1525; Nardi-Agmon, I. et al., J. Thorac. Oncol. 2016, 11, 827-837; Peled, N. et al., Nanomedicine (N.Y., NY, U. S.) 2013, 9, 758-766; Shuster, G. et at, Breast Cancer Res. Treat. 2011, 126, 791-796; Xu, Z. Q. et al., Br. J. Cancer 2013, 108, 941-950]. So far, most of the studies in the field have focused on binary comparisons, where a specific disease is compared to the corresponding (healthy) controls. Particularly, in the above-mentioned studies, disease detection was mostly carried out with reference to healthy control groups, without examining correlated and uncorrelated clinical confounding factors. Clinical classification itself was beyond the focus of said studies.

Patents and Patent Applications U.S. Pat. Nos. 8,366,630, 8,481,324, 8,597,953, 8,945,935, 8,999,244, 9,359,197, US 2012/0245854, US 2013/0150261, US 2013/0236981, WO 2010/079490 and WO 2011/083473, to some of the inventors of the present application disclose systems based on arrays of chemically sensitive sensors, for detecting volatile organic compounds derived from a breath sample, particularly for diagnosis of individual diseases and disorders, including lung cancer, breast cancer, head and neck cancer, prostate cancer, colon cancer, renal insufficiencies, Alzheimer's disease, Parkinson's disease and Multiple Sclerosis.

However, to the inventors' best knowledge, a universal sensor array providing diagnosis of various diseases and allowing efficient differentiation between said diseases, has never been reported. Additionally, while several sets of volatile organic compounds ware found to be indicative of a particular disease, no single set of VOCs, which would enable diagnosis and differentiation between numerous diseases and different classes of diseases is presently known.

Thus, there exists an unmet need for a reliable universal system and a method based on breath analysis, which would be capable of differentially diagnosing various diseases, instead of a single disease or a single class of diseases.

SUMMARY OF THE INVENTION

The present invention provides a system and methods for diagnosing, screening or monitoring a disease in a subject. The diseases diagnosable by the system and methods of the present invention include, inter alia, various neurodegenerative, renal, respiratory and inflammatory bowel diseases, and different types of cancers.

The present invention is based in part on a surprising finding that a carefully selected combination of VOCs, measured in an exhaled breath of a test subject allows diagnosis of a plurality of diseases in a subject and differentiation between said diseases instead of merely providing information on a single disease. Said universal biomarker set, which allows identification of a plurality of diseases, has been utilized by the inventors of the present invention to produce a universal diagnosis system based on cross-reactive nanoarray sensors, which are responsive to the VOCs of the universal biomarker set, which are combined with a pattern recognition analyzer. It was unexpectedly found that as few as three distinct sensors used within the universal system were capable of differentially diagnosing a plurality of diseases. The selected sensors, as combined, were able to distinguish between each two different diseases from the above list with adequate reliability and efficiency. Response patterns of the selected sensors to a variety of diseases are assembled into a database and patterns characteristic of the particular diseases are compiled. Response signals obtained from the selected sensors exposed to a breath sample of a subject afflicted with an unknown disease can thus be compared to a response pattern, characteristic of a particular disease, which is derived from said database of response patterns. Thus, instead of diagnosing one particular disease and differentiating between subjects afflicted with said disease and healthy subjects, the present invention allows identification and differentiation between multiple diseases in an exhaled breath of a test subject, using one universal diagnosing system based on nanoarray sensors, by measuring their response signals to the exhaled breath of the test subject and comparing them to disease specific patterns of said sensors.

Such universal diagnosing system also has an improved specificity, as compared to some previously known sensor nanoarray-based systems, which can detect only one disease. The disease-specific sensor systems are not configured to distinguish between different diseases. At least some of the VOCs which are characteristic to said specific disease can be common to a different type of disease. Accordingly, if a test subject is afflicted with a different disease which is not intended to be diagnosed by said disease-specific sensor system, but has a VOCs signature, which is at least partially similar to the signature of the designated disease, the sensor nanoarray would detect the VOCs of the different disease, resulting in a false positive response. In contrast, the universal diagnosing system of the present invention is designed to discriminate between different diseases, based on the disease-specific response patterns of the single set of selected sensors, thereby significantly reducing the risk of false positive diagnosis. The inventors have further found that the detection of one disease does not screen out other diseases, which might result in false negative results. Hence, the universal diagnosing system of the present invention allows detection of more than one disease in a subject.

Thus, according to one aspect, the present invention provides a system for diagnosing, screening or monitoring a disease in a test subject, the system comprising: a selected definitive sensor set comprising at least three sensors reactive to the presence of volatile organic compounds (VOCs) in an exhaled breath of the test subject, the sensors comprising nanomaterials selected from metal nanoparticles coated with a first organic coating and single walled carbon nanotubes (SWCNTs) coated with a second organic coating and a processing unit comprising a pattern recognition analyzer, wherein the pattern recognition analyzer receives output signals of the sensor set; compares them to disease-specific patterns derived from a database of response patterns of the sensor set to exhaled breath of subjects with known diseases, wherein each of the disease-specific patterns is characteristic of a particular disease, selected from the group consisting of neurodegenerative diseases, proliferative diseases, renal diseases, respiratory diseases, inflammatory bowel diseases and obstetric diseases; and selects a closest match between the output signals of the sensor set and the disease-specific patterns.

According to some embodiments, the selected definitive sensor set provides differentiation between two diseases, selected from the group consisting of neurodegenerative diseases, proliferative diseases, renal diseases, respiratory diseases, inflammatory bowel diseases and obstetric diseases, with an accuracy of at least about 80%. According to further embodiments, the selected definitive sensor set provides differentiation between two diseases selected from the group consisting of Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease and pre-eclampsia with an accuracy of at least about 80%.

Said differentiation between two diseases can be performed with at least one algorithm selected from the group consisting of discriminant function analysis (DFA), artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), linear discriminant analysis (LDA), cluster analysis, and nearest neighbor. Each possibility represents a separate embodiment of the present invention. In one embodiment, the at least one algorithm is discriminant function analysis (DFA).

In some embodiments, the metal nanoparticles are selected from the group consisting of Au, Ag, Ni, Co, Pt, Pd, Cu, and Al nanoparticles. Each possibility represents a separate embodiment of the present invention. In one embodiment, the metal nanoparticles are Au nanoparticles.

In some embodiments, the first organic coating comprises compounds selected from the group consisting of alkylthiols, arylthiols, alkylarylthiols, alkylthiolates, ω-functionalized alkanethiolates, arenethiolates, (γ-mercaptopropyl)trimethyloxysilane, dialkyl disulfides and combinations and derivatives thereof. Each possibility represents a separate embodiment of the present invention. In particular embodiments, the first organic coating comprises compounds selected from the group consisting of alkylthiols, arenethiolates, and combinations thereof.

The first organic coating can include a monolayer or multiple layers of organic compounds. Each possibility represents a separate embodiment of the invention. In some embodiments, the first organic coating comprises 1-6 layers of organic compounds.

The metal nanoparticles can have a morphology selected from a cubic, a spherical, and a spheroidal morphology. Each possibility represents a separate embodiment of the invention. In one embodiment, the nanoparticles have a spherical morphology.

In some embodiments, the metal nanoparticles coated with a first organic coating are configured in form of a film. The film thickness can be in the range from about 1 nm to about 500 nm.

In some embodiments, the second organic coating comprises polycyclic aromatic hydrocarbon (PAH). In further embodiments, the polycyclic aromatic hydrocarbon comprises hexa-perihexabenzocoronene (HBC) or a derivative thereof. The hexa-perihexabenzocoronene molecules can be unsubstituted or substituted by at least one of methyl ether (HBC—$OC_1$), 2-ethyl-hexyl (HBC—$C_{6,2}$), 2-hexyldecane (HBC—$C_{10,6}$), 2-decyl tetradecane (HBC—$C_{14,10}$), and dodecane (HBC—$C_{12}$). Each possibility represents a separate embodiment of the invention. In particular embodiments, the second organic coating comprises methyl ether-substituted HBC (methoxy hexa-perihexabenzocoronene). The methyl ether-substituted HBC can be in a hexagonal or a semi-triangular form. Each possibility represents a separate embodiment of the invention.

In other embodiments, the second organic coating comprises compounds selected from propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$), dioctyl phthalate ($C_{24}H_{38}O_4$), 1,2,5,6,9,10-hexabromo-cyclododecane ($C_{12}H_{18}Br_6$), pentadecane ($C_{15}H_{32}$), and combinations thereof. Each possibility represents a separate embodiment of the invention.

The single walled carbon nanotubes can be organized in a random network configuration. In some embodiments, the single walled carbon nanotubes have diameters ranging from about 0.9 nanometer (nm) to about 5 nanometers, and lengths ranging from about 1 micrometer (μm) to about 50 micrometers. Each possibility represents a separate embodiment of the invention.

According to some embodiments, the definitive sensor set includes at least three Au nanoparticle sensors. According to further embodiments, the definitive sensor set includes Au nanoparticles coated with dodecanethiol, Au nanoparticles coated with 1-decanethiol and Au nanoparticles coated with 3-ethoxythiophenol.

In some embodiments, the definitive sensor set includes at least four sensors. In some embodiments, the definitive sensor set includes at least five sensors. Optionally, the definitive sensor set can include at least six sensors. In some embodiments, the definitive sensor set includes at least seven sensors.

According to some embodiments, the definitive sensor set further includes Au nanoparticles coated with octadecanethiol and Au nanoparticles coated with 4-chlorobenzene methanethiol. In further embodiments the definitive sensor set further includes Au nanoparticles coated with hexanethiol. In additional embodiments, the sensor set further includes SWCNTs coated with methoxy hexa-perihexabenzocoronene.

The at least three sensors of the definitive sensor set can be configured in a form selected from the group consisting of a capacitive sensor, a resistive sensor, an impedance sensor, and a field effect transistor sensor. Each possibility represents a separate embodiment of the present invention.

According to some embodiments, the system further comprises a device which detects the sensor set responses to the exhaled breath of the test subject. According to further embodiments, the device measures the output signals of the sensor set upon exposure to the breath sample. In further embodiments, the pattern recognition analyzer receives output signals of the sensor set, measured by said device. In some embodiments, the device measures changes in at least one property of the sensor set, selected from the group consisting of resistance, conductance, alternating current (AC), frequency, capacitance, impedance, inductance, mobility, electrical potential, optical property and voltage threshold. Each possibility represents a separate embodiment of the present invention. In particular embodiments, the device measures changes in resistance or conductance of the sensors.

According to some embodiments, the pattern recognition analyzer receives at least two response induced parameters extracted from the output signals of the sensor set. The response induced parameters can be selected from the group consisting of full non steady state response at the beginning of the signal, full non steady state response at the beginning of the signal normalized to baseline, full non steady state response at the middle of the signal, full non steady state response at the middle of the signal normalized to baseline, full non steady state response at the peak of the signal, full non steady state response at the peak of the signal normalized to baseline, full steady state response at the end of the signal, full steady state response at the end of the signal normalized to baseline, area under non steady state response, area under steady state response, the gradient of the response upon exposure to the test sample, the gradient of the response upon removal of the test sample, the time required to reach a certain percentage of the response upon exposure to the test sample, or the time required to reach a certain percentage of the response upon removal of the test sample. In particular embodiments, the pattern recognition analyzer receives response induced parameters including the normalized change of sensor's resistance at the full non steady state response at the middle of the signal normalized to baseline, the full non steady state response at the peak of the signal normalized to baseline, the full steady state response at the end of the signal normalized to baseline, and the area under steady state response.

According to some embodiments, the response patterns of the sensor set to exhaled breath of subjects with known diseases, stored in the database, comprise at least two response induced parameters extracted from the output signals of the sensor set. Said response induced parameters can be selected from the group consisting of full non steady state response at the beginning of the signal, full non steady state response at the beginning of the signal normalized to baseline, full non steady state response at the middle of the signal, full non steady state response at the middle of the signal normalized to baseline, full non steady state response at the peak of the signal, full non steady state response at the peak of the signal normalized to baseline, full steady state response at the end of the signal, full steady state response at the end of the signal normalized to baseline, area under non steady state response, area under steady state response, the gradient of the response upon exposure to the test sample, the gradient of the response upon removal of the test sample, the time required to reach a certain percentage of the response upon exposure to the test sample, or the time required to reach a certain percentage of the response upon removal of the test sample. In particular embodiments, the response patterns comprise response induced parameters including the normalized change of sensor's resistance at the full non steady state response at the middle of the signal normalized to baseline, the full non steady state response at the peak of the signal normalized to baseline, the full steady state response at the end of the signal normalized to baseline, and the area under steady state response.

According to some embodiments, the database comprises response patterns of the sensor set to exhaled breath of at least about 500 subjects suffering from a known disease, of which at least about 15% are diagnosed with a neurodegenerative disease, at least about 30% are diagnosed with a proliferative disease, at least about 5% are diagnosed with a renal disease, at least about 1% are diagnosed with a respiratory disease, and at least about 5% are diagnosed with an inflammatory bowel disease. The database can further include response patterns of the sensor set to exhaled breath of subjects diagnosed with pre-eclampsia.

According to some embodiments, the disease is selected from the group consisting of neurodegenerative diseases, proliferative diseases, renal diseases, respiratory diseases, inflammatory bowel diseases and obstetric diseases. The neurodegenerative disease can be selected from the group consisting of Multiple Sclerosis, Alzheimer's disease, and Parkinson's disease. In some embodiments, Parkinson disease includes idiopathic Parkinson or atypical Parkinsonism. The proliferative disease can be selected from the group consisting of lung cancer, colon cancer, head and neck cancer, ovarian cancer, bladder cancer, prostate cancer, kidney cancer, and gastric cancer. In further embodiments, the inflammatory bowel disease is selected from the group consisting of Crohn's disease, ulcerative colitis and irritable bowel syndrome. The respiratory disease can include pulmonary artery hypertension. The renal disease can include chronic kidney disease. The obstetric disease can include pre-eclampsia.

In another aspect there is provided a method of diagnosing, screening or monitoring a disease in a test subject, the method comprising the steps of: (a) providing a system according to the various embodiments of the present invention; (b) exposing the sensor set to an exhaled breath sample of the test subject; (c) measuring the output signals of the sensor set upon exposure to the breath sample; (d) comparing the output signals using a pattern recognition analyzer to the database-derived disease-specific patterns; and (e) selecting the closest match between the output signals of the sensor set and the database-derived disease-specific patterns.

According to some embodiments, the method provides diagnosing, screening or monitoring of a disease selected from neurodegenerative diseases, proliferative diseases, inflammatory bowel diseases, respiratory diseases, renal diseases and obstetric diseases. According to further embodiments, the method provides diagnosing, screening or monitoring of a disease selected from the group consisting of Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease, and pre-eclampsia. Each possibility represents a separate embodiment of the invention.

According to further embodiments, the method provides differentiation between two or more diseases selected from Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney failure and pre-eclampsia. Each possibility represents a separate embodiment of the invention. According to some embodiments, the method provides differentiation accuracy of at least about 80%.

According to some embodiments, the method provides diagnosis of at least one disease in a test subject. According to other embodiments, the method provides diagnosis of a plurality of diseases in a test subject, such as two, three or more diseases. Each possibility represents a separate embodiment of the invention.

According to some embodiments, the method comprises measuring the output signals of the sensor set upon exposure to the breath sample by a device which measures changes in at least one property of the sensor set, selected from the group consisting of resistance, conductance, alternating current (AC), frequency, capacitance, impedance, inductance, mobility, electrical potential, optical property and voltage threshold. Each possibility represents a separate embodiment of the present invention.

According to some embodiments, the method further comprises the step of concentrating the exhaled breath sample prior to step (b) using at least one of a breath concentrator and a dehumidifying unit.

In some embodiments, the sensor set detects at least 10 VOCs selected from 2-ethylhexanol, 3-methylhexane, 5-ethyl-3-methyl-octane, acetone, ethanol, ethyl acetate, ethylbenzene, isononane, isoprene, nonanal, styrene, toluene and undecane. In further embodiments, the sensor set detects each of said VOCs.

According to some embodiments, the step of selecting the closest match between the output signals of the sensor set and the database-derived disease-specific patterns is performed by using at least one algorithm selected from the group consisting of discriminant function analysis (DFA), artificial neural network (ANN) algorithm, support vector machine (SVM), principal component analysis (PCA), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, and nearest neighbor. Each possibility represents a separate embodiment of the present invention. In certain embodiments, said algorithm is DFA.

In another aspect, the present invention provides a method of diagnosing, screening or monitoring a disease in a test subject, comprising the steps of: (a) collecting a test breath sample from the test subject; (b) determining levels of at least 10 volatile organic compounds (VOCs) from a universal biomarker set, the set including 2-ethylhexanol, 3-methylhexane, 5-ethyl-3-methyl-octane, acetone, ethanol, ethyl acetate, ethylbenzene, isononane, isoprene, nonanal, styrene, toluene and undecane; (c) comparing the levels of said VOCs from the test breath sample with reference levels of said VOCs derived from a database of said VOCs detected in exhaled breath of subjects with known diseases, wherein the combination of the reference levels of each of the VOCs of the universal biomarker set is characteristic of a particular disease, selected from the group consisting of neurodegenerative diseases, proliferative diseases, renal diseases, respiratory diseases, inflammatory bowel diseases, and obstetric diseases; and (d) selecting a closest match between the levels of said VOCs from the test breath sample and the combination of the reference levels of the VOCs of the universal biomarker set. According to some embodiments, the method comprises determining levels of each VOC from the universal biomarker set.

In some embodiments, the step of determining the levels of the VOCs comprises the use of at least one technique selected from the group consisting of Gas-Chromatography (GC), GC-lined Mass-Spectrometry (GC-MS), Proton Transfer Reaction Mass-Spectrometry (PTR-MS), Electronic nose device, and Quartz Crystal Microbalance (QCM). Each possibility represents a separate embodiment of the invention. In one embodiment, the step of determining the levels of the VOCs comprises the use of Gas-Chromatography-Mass Spectrometry (GC-MS). Optionally, the GC-MS can be combined with solid phase microextraction (SPME).

According to some embodiments, the disease is selected from the group consisting of neurodegenerative diseases, proliferative diseases, renal diseases, respiratory diseases, inflammatory bowel diseases and obstetric diseases. The neurodegenerative disease can be selected from the group consisting of Multiple Sclerosis, Alzheimer's disease, and Parkinson's disease. In some embodiments, Parkinson disease includes idiopathic Parkinson or atypical Parkinsonism. The proliferative disease can be selected from the group consisting of lung cancer, colon cancer, head and neck cancer, ovarian cancer, bladder cancer, prostate cancer, kidney cancer, and gastric cancer. In further embodiments, the inflammatory bowel disease is selected from the group consisting of Crohn's disease, ulcerative colitis and irritable bowel syndrome. The respiratory disease can include pulmonary artery hypertension. The renal disease can include chronic kidney disease. The obstetric disease can include pre-eclampsia.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A—Nonanal, FIG. 1B— Undecane and FIG. 1C— Isononane. The whisker boxes present 1st quartile, 3rd quartile, median (line) and average (square); the bars represent the 10% and 90% points, while the dots represent the minimal and maximal readings.

DETAILED DESCRIPTION OF THE INVENTION

Figure 1A:
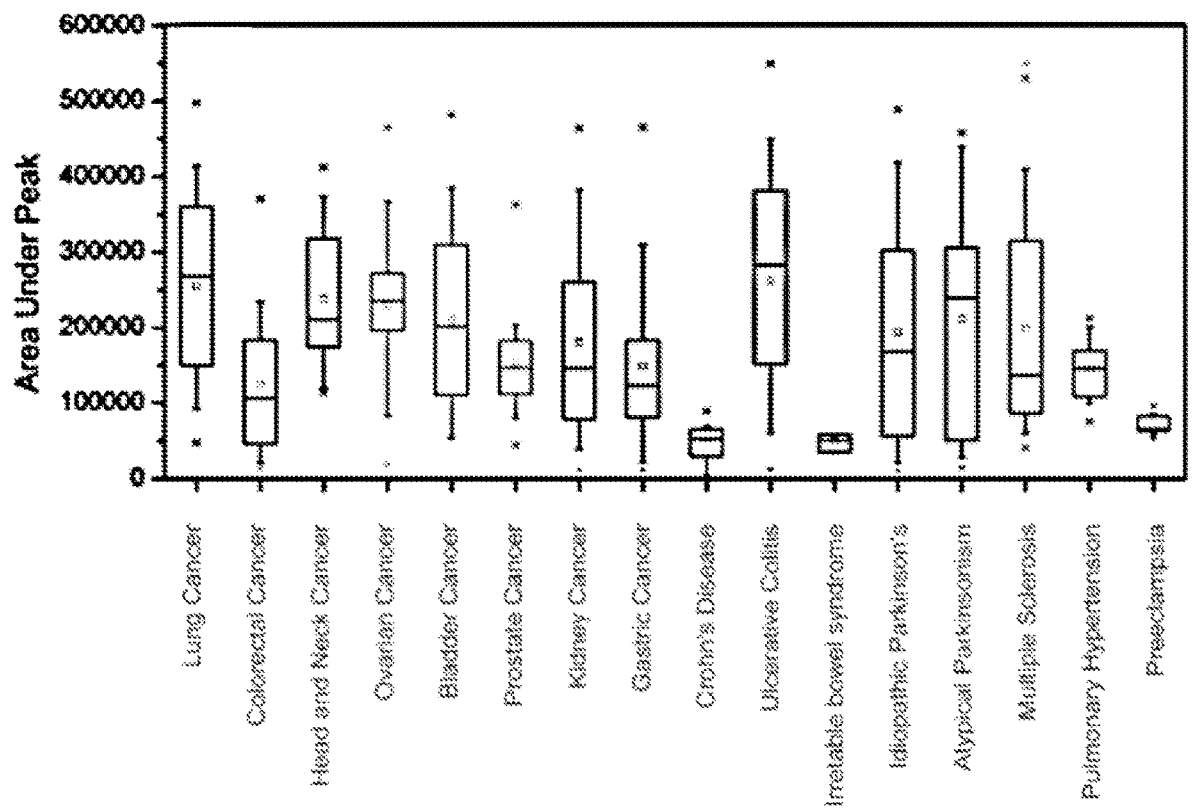
FIGS. 1A-1C: GC-MS analysis of the breath samples represented as area under peak (abundance) measured in different diseases of three representative VOCs.

The present invention provides a system and methods for diagnosing a variety of diseases, including inter alia, neurodegenerative diseases, proliferative diseases, renal diseases, respiratory diseases, and inflammatory bowel diseases.

The system and methods of the present invention provide a unique ability to diagnose a vast variety of diseases, while successfully differentiating between distinct classes of diseases and diseases within the same class and/or different classes. The present invention is based in part on the surprising results from 14 departments in 9 clinical centers worldwide, which showed that while each disease has its own unique volatile molecular print pattern, including hundreds of VOCs, detection of a particular combination of a relatively small number of VOCs allows differential diagnosis of each of said diseases. The test population included patients diagnosed with various neurodegenerative diseases, proliferative diseases, inflammatory bowel diseases, respiratory diseases, renal diseases and obstetric diseases. Analysis of the breath samples obtained from this test population allowed to identify a universal biomarker set, which provided differential diagnosis of each of said diseases. It was found that no one of the VOCs of this universal biomarker set, when analyzed alone, and no any other combination of the VOCs present in the tested breath samples was able to provide differential diagnosis with adequate efficiency.

It has been further discovered that the presence of one disease, detected by measuring the levels of said VOCS from the definitive set, did not screen out other diseases— the finding which allowed development of a universal system for personalized diagnosis and screening of various diseases in noninvasive, inexpensive and portable manner. The universal diagnosis system of the present invention is thus capable of detecting multiple diseases in the same test subject.

The universal diagnosis system included cross-reactive nanoarray sensors, which are reactive to the presence of VOCs in an exhaled breath of a test subject in combination with a pattern recognition analyzer. It has been unexpectedly found that as few as three such sensors were capable of differentially distinguishing between each two diseases of the examined diseases list. Said sensors included nanomaterials, selected from metal nanoparticles coated with an organic coating (e.g. mercapto derivatives) and single walled carbon nanotubes coated with a different organic coating (e.g. hexa-perihexabenzocoronene molecules).

This approach provided collective VOC patterns, which do not require specific VOC identification and quantification. Without wishing to being bound by theory or mechanism of action, the ability of the universal diagnosing system of the present invention to identify a plurality of diseases and to distinguish between them is based in part of the ability of the sensor set to detect the VOCs from the universal biomarker set and to produce a response pattern, which is characteristic of a particular disease.

It has been further found that analyzing more than one response induced parameter extracted from the response signal of said definitive set of sensors enhanced the differentiation efficiency of the system. The database of response patterns of said definitive set of sensors to breath samples of subjects afflicted with a particular disease is used by the inventors of the present invention to compile disease specific patterns characteristic of each of the diseases, which are detectable by said sensor set. The disease specific patterns are used by the pattern recognition analyzer according to the principles of the present invention to find the closest match between the response signals obtained from the exposure of the sensors set to the test breath samples and the empirical response pattern from the database.

Thus, according to one aspect, the present invention provides a system for diagnosing, screening and/or monitoring a disease in a test subject, the system comprising a selected definitive sensor set comprising at least three sensors reactive to the presence of volatile organic compounds (VOCs) in an exhaled breath of the test subject, the sensors comprising nanomaterials selected from the group consisting of metal nanoparticles coated with a first organic coating and single walled carbon nanotubes (SWCNTs) coated with a second organic coating. The system of the invention further comprises a processing unit comprising a pattern recognition analyzer, wherein the pattern recognition analyzer receives output signals of the sensor set; compares them to disease-specific patterns derived from a database of response patterns of the sensor set to exhaled breath of subjects with known diseases, wherein each of the disease-specific patterns is characteristic of a particular disease, and selects a closest match between the output signals of the sensor set and the disease-specific pattern.

In another aspect, the present invention provides a method of diagnosing, screening and/or monitoring a disease in a test subject using a system according to the principles and various embodiments of the present invention. The sensor set is exposed to an exhaled breath sample of the test subject and the output signals are compared, using a pattern recognition analyzer, to the database-derived disease-specific patterns in order to select the closest match between the output signals of the sensor set and the database-derived disease-specific patterns.

In some embodiments, the system and/or method of the invention provide diagnosing of the disease. In some embodiments, the system and/or method of the invention provide screening of the disease. In some embodiments, the system and/or method of the invention provide monitoring of the disease. Monitoring the disease by the system of the invention is particularly advantageous, when the patient is afflicted by more than one disease, as evaluating the progression of one disease is not affected by the presence of additional diseases. According to some embodiments, diagnosing, screening or monitoring of a disease in a subject is performed even in the presence of at least one confounding factor, such as, but not limited to, smoking. Furthermore, diagnosing, screening or monitoring of a disease in the same subject can be performed at various geographical locations, including a hospital, clinic or even at home, since no effect of the geographical location on the response of the sensor set was found.

According to some embodiments, the disease to be diagnosed, screened, and/or monitored and/or the disease from the presence of which the disease-specific pattern is derived is selected from the group consisting of neurodegenerative diseases, proliferative diseases, renal diseases, respiratory diseases, inflammatory bowel diseases and obstetric diseases. The neurodegenerative disease can be selected from the group consisting of Multiple Sclerosis, Alzheimer's disease, and Parkinson's disease. In some embodiments, Parkinson disease includes idiopathic Parkinson or atypical Parkinsonism. The proliferative disease can be selected from the group consisting of lung cancer, colon cancer, head and neck cancer, ovarian cancer, bladder cancer, prostate cancer, kidney cancer, and gastric cancer. In further embodiments, the inflammatory bowel disease is selected from the group consisting of Crohn's disease, ulcerative colitis and irritable bowel syndrome. The respiratory disease can include pulmonary artery hypertension. The renal disease can include chronic kidney disease. The obstetric disease can include pre-eclampsia. The terms "pre-eclampsia", toxemia", and "pre-eclampsia-toxemia" are used interchangeably throughout the specification.

According to some embodiments, the selected definitive set of sensors comprises metal nanoparticles comprising conductive metal cores which are coated with a first organic coating. Suitable non-limiting examples of conductive metal cores include, but are not limited to, Au, Ag, Ni, Co, Pt, Pd, Cu, and Al nanoparticles. Each possibility represents a separate embodiment of the invention.

In one embodiment, the coating of the conductive nanoparticle cores comprises a monolayer or multilayers of organic compounds, wherein the organic compounds can be small molecules, monomers, oligomers or polymers. Each possibility represents a separate embodiment of the present invention. Suitable organic compounds include, but are not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, □-functionalized alkanethiolates, arenethiolates, (γ-mercaptopropyl)tri-methyloxysilane, dialkyl disulfides and combinations thereof. Each possibility represents a separate embodiment of the present invention.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In a currently preferred embodiment, the alkyl group has 3-24 carbons designated here as $C_3$-$C_{24}$ alkyl. The alkyl group may be unsubstituted or substituted by one or more groups selected from alcohol, ketone, aldehyde, halogen, carbonate, carboxylate, carboxylic acid, acyl, amido, amide, amine, imine, ester, ether, cyano, nitro, and azido. Each possibility represents a separate embodiment of the present invention.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halogen, haloalkyl, ($C_1$-$C_8$)alkyl, ($C_2$-$C_8$) alkenyl, ($C_2$-$C_8$)alkynyl, ($C_6$-$C_{10}$)aryl, alcohol, ketone, aldehyde, carbonate, carboxylate, carboxylic acid, acyl, amido, amide, amine, imine, ester, ether, cyano, nitro, azido, and the like. Each possibility represents a separate embodiment of the present invention.

In particular embodiments, the first organic coating comprises compounds selected from arenethiolates, alkylarylthiols and combinations thereof. Each possibility represents a separate embodiment of the present invention. In further embodiments, the first organic coating includes compounds selected from dodecanethiol, 1-decanethiol, 3-ethoxythiophenol, octadecanethiol, and 4-chlorobenzene methanethiol. In some exemplary embodiments, the definitive sensor set comprises metal nanoparticles coated with dodecanethiol, 1-decanethiol, 3-ethoxythiophenol, octadecanethiol, 4-chlorobenzene methanethiol, and hexanethiol.

In further particular embodiments, the first organic coating comprises compounds selected from the group consisting of alkylthiols, arenethiolates, and combinations thereof. Each possibility represents a separate embodiment of the present invention. In certain such embodiments, the first organic coating can be at least one of dodecanethiol, 1-decanethiol and 3-ethoxythiophenol. In some exemplary embodiments, the definitive sensor set comprises metal nanoparticles coated with dodecanethiol, 1-decanethiol and 3-ethoxythiophenol.

In some embodiments, the first organic coating comprises a monolayer of organic compounds. In further embodiments, the first organic coating comprises two, three, four, five, six, seven, eight, nine, ten or more layers of organic compounds. Each possibility represents a separate embodiment of the invention. In further embodiments, the first organic coating comprises 1-6 layers of organic compounds.

In some embodiments, the first organic coating comprises 1-10 layers of hexanethiol. In further embodiments, the first organic coating comprises 1-6 layers of hexanethiol. In some embodiments, the first organic coating comprises one layer of hexanethiol, two layers of hexanethiol, three layers of hexanethiol, four layers of hexanethiol, five layers of hexanethiol, or six layers of hexanethiol. Each possibility represents a separate embodiment of the invention.

Sensors comprising metal nanoparticles capped with various organic coatings can be synthesized as is known in the art, for example using the two-phase method (Brust et al., J. Chem. Soc. Chem. Commun., 1994, 801, 2) with some modifications (Hostetler et al., Langmuir, 1998, 14, 24). Capped gold nanoparticles can be synthesized by transferring $AuCl_4^-$ from aqueous $HAuCl_4.xH_2O$ solution to a toluene solution by the phase-transfer reagent TOAB. After isolating the organic phase, excess thiols are added to the solution. The mole ratio of thiol:$HAuCl_4.xH_2O$ can vary between 1:1 and 10:1, depending on the thiol used. This is performed in order to prepare mono-disperse solution of gold nanoparticles in average size of about 2-5 nm. Exemplary procedures include, but are not limited to, thiol:Au mole ratios of 1:10 for dodecanethiol, 1-decanethiol and 3-ethoxythiophenol-capped gold nanoparticles, at an average size of 3-4 nm. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with particular thiols, such as, for example, 2-mercaptobenzoazole or 2-mercaptobenzimidazole can be synthesized by ligand—exchange method from pre-prepared hexanethiol-capped gold nanoparticles. In a typical reaction, excess of thiol is added to a solution of hexanethiol-capped gold nanoparticles in toluene. The solution is kept under constant stirring for few days in order to allow as much ligand conversion as possible. The nanoparticles are purified from free thiol ligands by repeated extractions.

The metal nanoparticles may have any desirable morphology including, but not limited to, a cubic, a spherical, and a spheroidal morphology. Each possibility represents a separate embodiment of the invention. In some embodiments, the metal nanoparticles have a spherical morphology. In some embodiments, the metal nanoparticles have a cubic morphology.

According to some embodiments, the mean particle size of the metal nanoparticles is in the range of about 1 to about 10 nm, such as, for example, about 2 to about 5 nm or about 3 to about 4 nm. Each possibility represents a separate embodiment of the invention. According to further embodiments, the metal nanoparticles are characterized by a narrow particle size distribution.

The synthesized nanoparticles can then be assembled (e.g. by a self-assembly process) to produce a film of capped nanoparticles. The term "film", as used herein, corresponds to a configuration of well-arranged assembly of capped nanoparticles. 2D or 3D films of coated nanoparticles may also be used. Exemplary methods for obtaining well-ordered two or three dimensional assemblies of coated nanoparticles include, but are not limited to, i. Random deposition from solution of capped nanoparticles on solid surfaces. The deposition is performed by drop casting, spin coating, spray coating and other similar techniques.
ii. Field-enhanced or molecular-interaction-induced deposition from solution of capped nanoparticles on solid surfaces.
iii. Langmuir-Blodgett or Langmuir-Schaefer techniques. The substrate is vertically plunged through self-organized/well-ordered 2D monolayer of capped nanoparticles at the air-subphase interface, wherein the latter is being subsequently transferred onto it. Multiple plunging of the substrate through the 2D monolayer of capped nanoparticles at the air-subphase interface results in the fabrication of the 3D-ordered multilayers of capped nanoparticles.
iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating capped nanoparticles from nanometer-scale to a mesoscopic scale (Zhao et al., J. Mater. Chem., 1997, 7(7), 1069).
v. Various combinations of Langmuir-Blodgett or Langmuir-Schaefer methods with soft lithographic techniques can be used to produce patterned Langmuir-Blodgett films of molecularly modified capped nanoparticles which are transferred onto solid substrates.
vi. Printing on solid-state or flexible substrates using an inject printer designated for printed electronics. A solution containing the capped nanoparticles is used as a filling material (or "ink") of the printing head according to procedures well known in the art.

Different experimental conditions and/or different deposition techniques of the nanoparticles solution upon the solid surface and/or substrate can result in different distribution/surface coverage of the sensor. The nanoparticle films can have continuous or discontinuous morphologies. In some embodiments, the system of the present invention comprises sensors having nanoparticle films with a continuous morphology, a discontinuous morphology or a combination of continuous or discontinuous morphologies. Each possibility represents a separate embodiment of the invention. According to some embodiments, control over the morphology of the nanoparticles film can alter the response of the sensor to the VOCs in the exhaled breath of the subject.

According to some embodiments, the system of the present invention comprises sensors, which contain metal nanoparticles coated with the same first coating but having different morphologies of the nanoparticles distribution on the substrate.

The thickness of the film of the present invention typically ranges from about 1 nm to about 500 nm. The film is typically deposited on top of a solid surface and/or substrate. Suitable substrates within the scope of the present invention include substances which may be rigid or flexible. Within the scope of the preset invention are flexible substrates which may also be stretchable. Exemplary substrates include, but are not limited to, metals, insulators, semiconductors, semimetals, polymers, and combinations thereof. Each possibility represents a separate embodiment of the present invention. In some embodiments, the substrate is a polymer which may be polyimide (e.g. Kapton), polyamide, polyimine (e.g. polyethylenimine), polyester (e.g. polyethylene terephthalate, polyethylene naphthalate), polydimethylsiloxane, polyvinyl chloride (PVC), polystyrene and the like. Each possibility represents a separate embodiment of the present invention. In one embodiment, the substrate comprises silicon dioxide (for example glass or a silicon wafer coated with $SiO_2$). In another embodiment, the substrate comprises indium tin oxide.

According to one embodiment, the sensor set comprises single-walled carbon nanotubes (SWCNTs) coated with a second organic coating. The nanotubes can be arranged in a random network configuration. In some embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The silicon wafer having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are currently available from commercial sources.

Other CVD methods include the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotube" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about 250 nm to about 1 mm Even more preferably, the single-walled carbon nanotubes have diameters ranging from about 0.8 nm to about 10 nm and lengths ranging from about 0.5 micrometer (µm) to about 100 µm. Most preferably, the single-walled carbon nanotubes of the present invention have diameters ranging from about 0.9 nm to about 5 nm and lengths ranging from about 1 µm to about 50 µm.

According to the principles of the present invention, the single walled carbon nanotubes are coated with a second organic coating comprising small molecules, oligomers, polymers or combinations thereof. In some embodiments, the second organic coating comprises molecules including, but not limited to, unsubstituted or substituted $C_1$-$C_{40}$ linear or branched alkanes, cycloalkanes, aromatic compounds, and combinations thereof. Each possibility represents a separate embodiment of the present invention. The molecules may be substituted by at least one of a carboxyl, an acyl, an ester, a nitro, a halogen, a hydroxyl or a haloalkyl moiety. Each possibility represents a separate embodiment of the present invention. Suitable small organic molecules include, but are not limited to, propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$), dioctyl phthalate ($C_{24}H_{38}O_4$), 1,2,5,6,9,10-hexabromo-cyclododecane ($C_{12}H_{18}Br_6$), pentadecane ($C_{15}H_{32}$), and combinations thereof. Each possibility represents a separate embodiment of the present invention.

Suitable oligomers or polymers include, but are not limited to, arenes, polyarenes or combinations thereof. As used herein the term "arene" refers to single as well as linked or fused aromatic rings which may be further substituted. The term "polyarene" as used herein refers to polycyclic aromatic hydrocarbons which comprise three or more rings, wherein at least two of which are aromatic and in which at least two of these aromatic rings are fused by sharing two adjacent carbon atoms. Suitable arenes or polyarenes include, but are not limited to, naphthalene, acenaphtene, anthracene, phenanthrene, pyrene, benzo[a]pyrene, chrysene, fluoranthene, $C_{18}$-$C_{180}$ graphenes and combinations thereof. Each possibility represents a separate embodiment of the present invention. The term "arene" further includes heteroarenes wherein one or more ring carbon atoms of the arene is replaced with a heteroatom (e.g., N, S, P or O), for example, phenyl-thiophenyl-phenyl-thiophenyl. Arenes may be non-functionalized (un-substituted) or may be functionalized with one or more substituents, for example hydrophobic or hydrophilic carbon chains. In addition, the arenes or the hydrophobic or hydrophilic carbon chains may be functionalized with least one functional group including, but not limited to, ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups. Each possibility represents a separate embodiment of the present invention.

One class of arenes or polyarenes within the scope of the present invention is $C_{18}$-$C_{180}$ graphenes, for example $C_{42}$ graphene, $C_{50}$ graphene and the like. The term "graphene" as used herein refers to a molecule in which a plurality of carbon atoms (e.g., in the form of five-membered rings, six-membered rings, and/or seven-membered rings) are covalently bound to each other to form a (typically sheet-like) polycyclic aromatic molecule. In one embodiment, the graphene comprises a single layer of carbon atoms that are covalently bound to each other (most typically $sp^2$ bonded). It should be noted that such sheets may have various configurations, and that the particular configuration will depend, inter alia, on the amount and position of five-membered and/or seven-membered rings in the sheet. In another embodiment, the graphene comprises several (e.g., two, three, four, five to ten, one to twenty, one to fifty, or one to hundred) single layers of carbon atoms which are stacked together to a maximum thickness of less than about 100 nanometers.

In some embodiments, the small organic molecules used to functionalize the surface of the nanotubes include, but are not limited to, polycyclic aromatic hydrocarbon derivatives, such as hexa-perihexabenzocoronene (HBC) molecules. HBC molecules can be unsubstituted or substituted by any one of methyl ether (HBC—$OC_1$), 2-ethyl-hexyl (HBC—$C_{6,2}$), 2-hexyldecane (HBC—$C_{10,6}$), 2-decyl tetradecane (HBC—$C_{14,10}$), and dodecane (HBC—$C_{12}$). Each possibility represents a separate embodiment of the invention. In particular embodiments, the second organic coating comprises methyl ether-substituted HBC (methoxy hexa-perihexabenzocoronene). The methyl ether-substituted HBC can be in a hexagonal or a semi-triangular form. Each possibility represents a separate embodiment of the invention.

According to some embodiments, the at least three nanosensors of the definitive sensor set are selected from the group consisting of metal nanoparticles coated with dodecanethiol, metal nanoparticles coated with 1-decanethiol, metal nanoparticles coated with 3-ethoxythiophenol, metal nanoparticles coated with octadecanethiol, metal nanoparticles coated with 4-chlorobenzene methanethiol, metal nanoparticles coated with hexanethiol and SWCNTs coated with substituted HBC.

According to some embodiments, the definitive sensor set includes Au nanoparticle sensors. According to some embodiments, said sensors are spherical. In further embodiments, the Au nanoparticles are configured in a form of a film. According to some embodiments, the films have continuous regions of the Au nanoparticles, discontinuous regions and combinations thereof.

According to further embodiments, the definitive sensor set includes Au nanoparticles coated with dodecanethiol, Au nanoparticles coated with 1-decanethiol and Au nanoparticles coated with 3-ethoxythiophenol. In some exemplary embodiments, these Au nanoparticles are spherical.

In some embodiments, the definitive sensor set includes at least four sensors. In some embodiments, the definitive sensor set includes at least five sensors. Optionally, the definitive sensor set can include at least six sensors. In other embodiments, the sensor set includes at least seven sensors. In further embodiments, the sensor set includes at least eight sensors.

According to some embodiments, the definitive sensor set includes Au nanoparticles coated with dodecanethiol, Au nanoparticles coated with 1-decanethiol, Au nanoparticles coated with 3-ethoxythiophenol, Au nanoparticles coated with octadecanethiol and Au nanoparticles coated with 4-chlorobenzene methanethiol. According to further embodiments, the definitive sensor set includes Au nanoparticles coated with dodecanethiol, Au nanoparticles coated with 1-decanethiol, Au nanoparticles coated with 3-ethoxythiophenol, Au nanoparticles coated with octadecanethiol, and Au nanoparticles coated with 4-chlorobenzene methanethiol. According to still further embodiments, the definitive sensor set includes Au nanoparticles coated with dodecanethiol, Au nanoparticles coated with 1-decanethiol, Au nanoparticles coated with 3-ethoxythiophenol, Au nanoparticles coated with octadecanethiol, Au nanoparticles coated with 4-chlorobenzene methanethiol, and Au nanoparticles coated with hexanethiol.

According to some embodiments, the definitive sensor set comprises SWCNTs coated with substituted hexa-perihexabenzocoronene. In further embodiments, the sensor set comprises SWCNTs coated with methoxy hexa-perihexabenzocoronene.

According to some embodiments, the definitive sensor set comprises a combination of metal nanoparticles coated with a first organic coating and single walled carbon nanotubes coated with a second organic coating. In certain such embodiments, the definitive sensor set can include Au nanoparticles coated with dodecanethiol, Au nanoparticles coated with 1-decanethiol, Au nanoparticles coated with 3-ethoxythiophenol and SWCNTs coated with HBC—$OC_1$. In some embodiments, the sensor set includes Au nanoparticles coated with dodecanethiol, Au nanoparticles coated with 1-decanethiol, Au nanoparticles coated with 3-ethoxythiophenol, Au nanoparticles coated with octadecanethiol, Au nanoparticles coated with 4-chlorobenzene methanethiol, and SWCNTs coated with HBC—$OC_1$. In further embodiments, the sensor set includes Au nanoparticles coated with dodecanethiol, Au nanoparticles coated with 1-decanethiol, Au nanoparticles coated with 3-ethoxythiophenol, Au nanoparticles coated with octadecanethiol, Au nanoparticles coated with 4-chlorobenzene methanethiol, Au nanoparticles coated with hexanethiol and SWCNTs coated with HBC—$OC_1$.

In certain embodiments, the sensors of the present invention comprise one or more conducting elements. According to some embodiments, the sensors of the present invention comprises a pair of electrodes (a positive electrode and a negative electrode) or a plurality of pairs of electrodes. In certain such embodiments, the amount of pairs of electrodes range between about 10 to about 100 pairs of electrodes. In additional embodiments, the amount of pairs of electrodes range between about 20 to about 50 pairs of electrodes. In still further embodiments, the amount of pairs of electrodes range between about 20 to about 30 pairs of electrodes. In various embodiments, the distance between adjacent electrodes between adjacent electrodes which defines the sensing area ranges between about 0.5 μm to about 3 mm According to certain embodiments, the width of each electrode ranges between about 1 μm to about 50 μm. The electrodes can comprise patterned electrodes, for example, interdigitated electrodes. In some embodiments, the sensors include a plurality of sets of interdigitated electrodes. The interdigitated electrodes can have any shape known in the art, such as, but not limited to circular or rectangular shapes. In certain embodiments, the spacing between adjacent electrodes of the interdigitated electrodes ranges between about 0.5 μm to about 3 mm. Alternatively, the electrodes may include a source and a drain electrode separated from one another by a source-drain gap. The system disclosed herein may further comprise a gate electrode wherein the sensor signal may be indicative of a certain property (e.g. resistance) of the nanomaterial under the influence of a gate voltage. Alternatively, the sensor signal may be indicative of a capacitance property of the nanomaterial. Within the scope of the present invention are sensors comprising continuous and discontinuous regions of metal nanoparticles coated with a first organic coating formed on a substrate comprising a plurality of electrodes (e.g. Au electrodes).

According to some embodiments, the sensor set is configured in a form of a capacitive sensor, a resistive sensor, an impedance sensor or a field effect transistor sensor. Each possibility represents a separate embodiment of the invention.

The output signal of the definitive sensor set may be induced, according to the principles of the present invention by a change in any one or more of conductivity, resistance, impedance, capacitance, inductance, or optical properties of sensors of the definitive sensor set upon exposure to the breath sample. In a particular embodiment, the sensor set output signal comprises a change in conductivity or resistance.

The output signal of the sensor set can be detected and/or measured by a detection device. Accordingly, in some embodiments, the system comprises a device which detects the sensor set responses to the exhaled breath of a test subject. According to some embodiments, the device measures the output signals of the sensor set upon exposure to the breath sample. In further embodiments, the pattern recognition analyzer receives output signals of the sensor set, measured by said device. Suitable devices include devices which are susceptible to a change in any one or more of resistance, conductance, alternating current (AC), frequency, capacitance, impedance, inductance, mobility, electrical potential, an optical property or voltage threshold. Each possibility represents a separate embodiment of the present invention. In additional embodiments, the device includes devices which are susceptible to swelling or aggregation of nanomaterials as well as devices which are susceptible to a change in any one or more of optical signal, fluorescence, chemiluminsence, photophorescence, bending, surface acoustic wave, piezoelectricity and the like. Each possibility represents a separate embodiment of the present invention. Changes in the electric properties of the sensor set, such as resistance, conductance, alternating current, capacitance, impedance, electrical potential, or voltage threshold can be measured by any suitable device known in the art, including, inter alia, a data logger, a potentiostat, a voltmeter, a conductivity meter, an LCR meter or a millimeter. Changes in the optical properties of the sensor set, including fluorescence, chemiluminsence, or photophorescence, can be measured by any suitable technique and/or device, such as but not limited to, spectroscopic ellipsometry, fluorescence spectroscopy or a luminometer. Changes in the piezoelectricity properties of the sensor set can be measured using, for example, a piezoelectric sensor.

According to some embodiments, the detection device comprises a device that measures changes in at least one property of the definitive sensor set, the device being selected from a resistance measurement device, a conductance measurement device, an alternating current measurement device, a frequency measurement device, a capacitance measurement device, an impedance measurement device, an inductance measurement device, a mobility measurement device, an electrical potential measurement device, an optical property measurement device, a voltage threshold measurement device, a fluorescence measurement device, a chemiluminsence measurement device, a phosphorescence measurement device, a bending measurement device, a surface acoustic wave measurement device, and a piezoelectricity measurement device.

According to some embodiments, the processing unit extracts a plurality of response-induced parameters from the output signal of the sensor set. Without wishing to being bound by theory or mechanism of action, extraction of the plurality of response induced parameters, also termed hereinbelow "sensing features", from the output signal of the sensor set allows to improve differentiation accuracy, sensitivity and/or specificity of the sensor set. Extracting a plurality of response induced parameters can further allow decreasing the minimal number of sensors in the sensor set required to provide the desired differentiation efficiency.

In some embodiments, the pattern recognition analyzer receives said plurality of response induced parameters extracted from the output signal of the sensor set. In some embodiments, the database of the response patterns and/or the disease-specific patterns derived from said database includes a plurality of response-induced parameters.

The plurality of response induced parameters can include at least two response induced parameters. According to other embodiment, the plurality of response induced parameters includes at least three response induced parameters, at least four response induced parameters, at least five response induced parameters, at least six response induced parameters, or at least seven response induced parameters. Each possibility represents a separate embodiment of the invention.

The response induced parameters can be selected from steady state normalized response, the time interval for obtaining steady state normalized response, and the time required to reach baseline after removal of the test sample. In some embodiments, the response induced parameters include full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the invention.

In particular embodiments, the response-induced parameters are selected from the group consisting of the normalized change of sensor's resistance at the full non steady state response at the middle of the signal normalized to baseline, the full non steady state response at the peak of the signal normalized to baseline, the full steady state response at the end of the signal normalized to baseline, and the area under steady state response. In certain embodiments, at least two of said response induced parameters are extracted from the output signals of the sensors of the sensor set. In certain embodiments, at least two of said response induced parameters are extracted from the output signals of each of the sensors of the sensor set. Optionally, at least three of said response-induced parameters are extracted from the output signals. In other embodiments, the response-induced parameters extracted from the output signal include the normalized change of sensor's resistance at the full non steady state response at the middle of the signal normalized to baseline, the full non steady state response at the peak of the signal normalized to baseline, the full steady state response at the end of the signal normalized to baseline, and the area under steady state response.

In certain embodiments, the database of the response patterns and/or the disease-specific patterns derived from said database includes at least two of said response induced parameters. Optionally, the database of the response patterns and/or the disease-specific patterns include at least three of said response-induced parameters In other embodiments, the database of the response patterns and/or the disease-specific patterns include the normalized change of sensor's resistance at the full non steady state response at the middle of the signal normalized to baseline, the full non steady state response at the peak of the signal normalized to baseline, the full steady state response at the end of the signal normalized to baseline, and the area under steady state response In another embodiment, the plurality of response induced parameters are extracted from the output signal of the sensor set, including a change in resistance, impedance, capacitance, inductance, conductivity, and optical properties of the sensor upon exposure thereof to the breath sample. Each possibility represents a separate embodiment of the invention. In a particular embodiment, the plurality of response induced parameters are extracted from a change in resistance or conductivity of the sensor.

According to the principles of the present invention, the pattern recognition analyzer analyzes the output signals of the sensor set. In some embodiments, the pattern recognition analyzer analyzes the plurality of response induced parameters extracted from the output signals of the sensor set.

In order to identify a particular disease in the exhaled breath sample, the output signals of the sensor set have to be compared to a reference. According to the principles of the present invention, the reference is a disease-specific pattern derived from a database of response patterns of the same selected definitive sensor set to exhaled breath of subjects with known diseases. Each reference, i.e., each disease-specific pattern is characteristic of a particular disease, selected from neurodegenerative diseases, proliferative diseases, renal diseases, respiratory diseases, and inflammatory bowel diseases. Thus, the pattern recognition analyzer receives output signals of the sensor set, wherein said output signals may include a plurality of response induced parameters extracted from said signal, compares them to the disease-specific patters derived from the database and selects a closest match between the output signals of the sensor set and the disease-specific pattern. In other words, the pattern recognition analyzer chooses the disease-specific pattern, which has the closest match with the output signals of the sensor set. The closest match selection can be performed by means of statistical classification. Statistical classification allows to identify to which of a set of categories (i.e., diseases) a new observation (i.e., output signals of the sensor set) belongs, on the basis of a training set of data containing observations whose category membership is known (i.e., disease-specific pattern). The new observations can be analyzed into a set of variables. For example, when comparing between each two sets of database samples, which belong to two different diseases, responses obtained from the sensor set can be processed and combined into one variable with new orthogonal axes, so called canonical values. Then for each group, the mean canonical value can be calculated, and used as a reference for test samples. When a test sample is analyzed by the pattern recognition analyzer, the same algorithm can be applied on the test sample, and the classification is determined according to the "distance" from the center/mean of each of the two groups. Alternatively, the set of variables can be compared to the set of variables extracted from all the disease-specific patterns simultaneously. Optionally, the new observations can be compared to the known observations by means of a similarity or distance function.

According to some embodiments, for the sake of statistical classification the pattern recognition analyzer utilizes an algorithm selected from but not limited to, artificial neural network (ANN) algorithm, support vector machine (SVM), and discriminant function analysis (DFA). Each possibility represents a separate embodiment of the present invention. In one embodiment, the pattern recognition analyzer utilizes discriminant factor analysis. By using a linear combination of the input variables DFA finds new orthogonal axes (canonical values), in a way that minimize the variance within each given class and maximize the variance between two classes. In another embodiment, the pattern recognition analyzer utilizes support vector machine algorithm. SVM is a supervised learning model with associated learning algorithms that analyze data and recognize patterns, used for classification and regression analysis. Given a set of training examples, each marked as belonging to one of two categories, an SVM training algorithm builds a model that assigns new examples into one category or the other, making it a non-probabilistic binary linear classifier.

The pattern recognition analyzer can utilize an algorithm selected from principal component analysis (PCA), multilayer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, and nearest neighbor. Each possibility represents a separate embodiment of the present invention.

Additional algorithms, which can be used in the systems and methods of the present invention, include Fisher linear discriminant analysis (FLDA), soft independent modeling of class analogy (SIMCA), K-nearest neighbors (KNN), genetic algorithms, and fuzzy logic algorithms and canonical discriminant analysis (CDA). According to some embodiments, prior to applying the algorithm to the measured response of the sensors, feasibility of the algorithm is evaluated by using the database of response patterns.

In some embodiments, the processing unit is a computer-controlled device. In some embodiments, the processing unit is a part of a computer. In some embodiments, the pattern recognition analyzer is a computer system configured for executing various algorithms stored on a non-transitory memory Other classification techniques that are known to those skilled in statistical data analysis can be used as well. Regardless of the classification technique that is used, the technique and its application in this context are readily susceptible to computerized implementation. After analysis is completed, the resulting information can be presented on a display or transmitted to a host computer. In certain embodiments, presenting the resulting information on a display or transmitting said information to a host computer using the processing unit. In some embodiments, the processing unit comprises a reporting unit that provides a quantitative signal for the output signals of the sensor set and/or the closest match between the output signals and the disease-specific pattern.

The term "closest match", relates in some embodiments, to a difference between the output signals of the sensor set and the disease specific-pattern, which is smaller than the difference between said output signals and any other disease-specific patterns. In other embodiments, the "closest match" relates to a difference in the absolute numerical values of the output signals and/or response induced parameters extracted from said response signals and the disease-specific pattern and/or response induced parameters extracted from said disease-specific pattern, which is lower than 10%, 5%, 1% or 0.5%. Each possibility represents a separate embodiment of the invention.

The database according to the principles of the present invention has to be sufficient to provide a reliable cumulative disease-specific pattern characteristic of a particular disease, selected from neurodegenerative diseases, proliferative diseases, renal diseases, respiratory diseases, and inflammatory bowel diseases, which would serve as a reference to allow differential diagnosis of a disease based on a comparison with said reference. Thus, according to some embodiments, the database includes response patterns of the sensor set to exhaled breath of at least 500 subjects. Optionally the database can include response patterns obtained from at least 600 subjects, 700 subjects, 800 subjects, 900 subjects or 1000 subjects. Each possibility represents a separate embodiment of the invention.

In some embodiments, at least a portion of said subjects suffer from a known disease. According to further embodiments, of said subjects at least about 15% are diagnosed with a neurodegenerative disease, at least about 30% are diagnosed with a proliferative disease, at least about 5% are diagnosed with a renal disease, at least about 1% are diagnosed with a respiratory disease, and at least about 5% are diagnosed with an inflammatory bowel disease. In some exemplary embodiments, about 22% of said subjects are diagnosed with a neurodegenerative disease, about 49% are diagnosed with a proliferative disease, about 10% are diagnosed with a renal disease, about 3% are diagnosed with a respiratory disease, and about 13% are diagnosed with an inflammatory bowel disease. The database can further include response patterns of the sensor set to exhaled breath of subjects diagnosed with obstetric diseases. In certain embodiments, the database includes response patterns of the sensor set to exhaled breath of subjects diagnosed with pre-eclampsia.

According to some embodiments, about 25% of the response patterns of the sensor set to exhaled breath of the patients afflicted with a neurodegenerative disease are obtained from patients having Parkinson's disease. According to some embodiments, about 25% of the response patterns of the sensor set to exhaled breath of the patients afflicted with a neurodegenerative disease are obtained from patients having Multiple Sclerosis.

According to some embodiments, about 5% of the response patterns of the sensor set to exhaled breath of the patients afflicted with a proliferative disease are obtained from patients having lung cancer. According to some embodiments, about 10% of the response patterns of the sensor set to exhaled breath of the patients afflicted with a proliferative disease are obtained from patients having colon cancer. According to some embodiments, about 3% of the response patterns of the sensor set to exhaled breath of the patients afflicted with a proliferative disease are obtained from patients having head and neck cancer. According to some embodiments, about 5% of the response patterns of the sensor set to exhaled breath of the patients afflicted with a proliferative disease are obtained from patients having ovarian cancer. According to some embodiments, about 10% of the response patterns of the sensor set to exhaled breath of the patients afflicted with a proliferative disease are obtained from patients having bladder cancer. According to some embodiments, about 1% of the response patterns of the sensor set to exhaled breath of the patients afflicted with a proliferative disease are obtained from patients having prostate cancer. According to some embodiments, about 4% of the response patterns of the sensor set to exhaled breath of the patients afflicted with a proliferative disease are obtained from patients having kidney cancer. According to some embodiments, about 15% of the response patterns of the sensor set to exhaled breath of the patients afflicted with a proliferative disease are obtained from patients having gastric cancer.

According to some embodiments, about 20% of the response patterns of the sensor set to exhaled breath of the patients afflicted with an inflammatory bowel disease are obtained from patients having Crohn's disease. According to some embodiments, about 20% of the response patterns of the sensor set to exhaled breath of the patients afflicted with an inflammatory bowel disease are obtained from patients having ulcerative colitis. According to some embodiments, about 15% of the response patterns of the sensor set to exhaled breath of the patients afflicted with an inflammatory bowel disease are obtained from patients having irritable bowel syndrome.

According to some embodiments, the database further includes response patterns of the sensor set to exhaled breath of healthy subjects. In certain embodiments, the database includes response patterns of the sensor set to exhaled breath of at least 50 healthy subjects, at least about 100 healthy subjects, at least about 200 healthy subjects, at least about 300 healthy subjects, at least about 400 healthy subjects, at least about 500 healthy subjects, or at least about 800 healthy subjects. Each possibility represents a separate embodiment of invention.

In some embodiments, the database includes response patterns of the sensor set to exhaled breath of at least about 500 subjects suffering from a known disease and at least about 100 healthy subjects. In further embodiments, the database includes response patterns of the sensor set to exhaled breath of at least about 500 subjects suffering from a known disease and at least about 500 healthy subjects. In additional embodiments, the database includes response patterns of the sensor set to exhaled breath of at least about 800 subjects suffering from a known disease and at least about 800 healthy subjects.

In certain embodiments, the disease-specific pattern comprises a response pattern of the sensors set to a combination of two or more diseases in a subject. Said combined pattern can be compiled based on the individual response patterns to distinct diseases or con be obtained from the sensors' responses to the breath samples of subjects afflicted with more than one disease.

According to some embodiments, the differential diagnosis efficiency of the system and methods of the present invention, utilizing said system, is expressed by the accuracy, sensitivity and/or specificity of differentiation between two diseases or between two classes of diseases. Each possibility represents a separate embodiment of the invention. Sensitivity and specificity are statistical measures of the performance of a binary classification test, also known in statistics as classification function. "Sensitivity", as used herein, refers to the proportion of actual positives which are correctly identified as such (e.g., the percentage of sick people who are correctly identified as having the condition or the percentage of sick people who are correctly identified as having the particular condition). Sensitivity is complementary to specificity. "Specificity", as used herein, refers to the proportion of negatives which are correctly identified as such (e.g., the percentage of healthy people who are correctly identified as not having the condition or the percentage of sick people not having the particular disease). "Accuracy", as used herein, refers to the proportion of the correctly identified positives and negatives out of the whole test population According to some embodiments, the selected definitive sensor set provides differentiation between two classes of diseases, selected from the group consisting of neurodegenerative diseases, proliferative diseases, renal diseases, respiratory diseases, and inflammatory bowel diseases, with an accuracy of at least 90%. According to further embodiments, the sensor set provides differentiation between said two classes of diseases with an accuracy of at least 92%, 95% or even 97%. Each possibility represents a separate embodiment of the invention. The neurodegenerative disease can be selected from the group consisting of Multiple Sclerosis, Alzheimer's disease, and Parkinson's disease. In some embodiments, Parkinson disease includes idiopathic Parkinson or atypical Parkinsonism. The proliferative disease can be selected from the group consisting of lung cancer, colon cancer, head and neck cancer, ovarian cancer, bladder cancer, prostate cancer, kidney cancer, and gastric cancer. In further embodiments, the inflammatory bowel disease is selected from the group consisting of Crohn's disease, ulcerative colitis and irritable bowel syndrome. The respiratory disease can include pulmonary artery hypertension. The renal disease can include chronic kidney disease. The obstetric disease can include pre-eclampsia.

According to further embodiments, the selected definitive sensor set provides differentiation between two diseases within one class of diseases with an accuracy of at least 80%. According to further embodiments, the sensor set provides differentiation between two diseases with an accuracy of at least 82%, 85%, 86%, 87%, 90%, 92% or even 95%. Each possibility represents a separate embodiment of the invention.

According to further embodiments, the selected definitive sensor set provides differentiation between two diseases selected from Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease and pre-eclampsia with an accuracy of at least 80%. According to further embodiments, the sensor set provides differentiation between two diseases with an accuracy of at least 82%, 85%, 86%, 87%, 90%, 92% or even 95%. Each possibility represents a separate embodiment of the invention. In certain embodiments, the sensor set provides differentiation between two diseases with an accuracy of 86%. In further embodiments, the sensor set provides differentiation between any two diseases with an accuracy of 86%.

According to some embodiments, the selected definitive sensor set provides differentiation between two classes of diseases, selected from the group consisting of neurodegenerative diseases, proliferative diseases, renal diseases, respiratory diseases, and inflammatory bowel diseases, with a sensitivity of at least 90%. According to further embodiments, the sensor set provides differentiation between said two classes of diseases with a sensitivity of at least 92%, 95% or even 97%. Each possibility represents a separate embodiment of the invention. According to still further embodiments, the selected definitive sensor set provides differentiation between two diseases within said class of diseases with a sensitivity of at least 80%. According to yet further embodiments, the sensor set provides differentiation between two diseases with a sensitivity of at least 82%, 85%, 86%, 87%, 90%, 92% or even 95%. Each possibility represents a separate embodiment of the invention. According to still further embodiments, the selected definitive sensor set provides differentiation between two diseases selected from Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease and pre-eclampsia with a sensitivity of at least 80%. According to yet further embodiments, the sensor set provides differentiation between any two diseases with a sensitivity of at least 82%, 85%, 86%, 87%, 90%, 92% or even 95%. Each possibility represents a separate embodiment of the invention.

According to some embodiments, the selected definitive sensor set provides differentiation between two classes of diseases, selected from the group consisting of neurodegenerative diseases, proliferative diseases, renal diseases, respiratory diseases, and inflammatory bowel diseases, with a selectivity of at least 90%. According to further embodiments, the sensor set provides differentiation between said two classes of diseases with a selectivity of at least 92%, 95% or even 97%. Each possibility represents a separate embodiment of the invention. According to still further embodiments, the selected definitive sensor set provides differentiation between two diseases within said class of diseases with a selectivity of at least 80%. According to yet further embodiments, the sensor set provides differentiation between two diseases with a selectivity of at least 82%, 85%, 86%, 87%, 90%, 92% or even 95%. Each possibility represents a separate embodiment of the invention. According to still further embodiments, the selected definitive sensor set provides differentiation between two diseases selected from Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease and pre-eclampsia with a selectivity of at least 80%. According to yet further embodiments, the sensor set provides differentiation between any two diseases with a selectivity of at least 82%, 85%, 86%, 87%, 90%, 92% or even 95%. Each possibility represents a separate embodiment of the invention.

According to some embodiments, the disclosed accuracy values correspond to an average value obtained from multiple differentiations between different pairs of diseases. According to some embodiments, the disclosed sensitivity values correspond to an average value obtained from multiple differentiations between different pairs of diseases. According to some embodiments, the disclosed specificity values correspond to an average value obtained from multiple differentiations between different pairs of diseases.

The differentiation between two classes of diseases, between two distinct diseases and/or between two diseases within the same class of diseases can be performed with at least one algorithm selected from artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), cluster analysis including nearest neighbor, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the invention. According to some embodiments, the reliability of the selected database can be evaluated by analyzing the database response patterns of subjects with known diseases, using said at least one algorithm. According to additional embodiments, the reliability of the selected definitive sensor set can be evaluated by analyzing the output signals from the sensor set to exhaled breath of subjects with known diseases, using said at least one algorithm.

In some experimental embodiments, the differentiation between two diseases or between sick and healthy subjects is performed by DFA. DFA is a supervised linear method that is supplied with the classification information regarding every measurement in the training set (Breteton R. Chemometrics, application of mathematics and statistics to laboratory systems Ellis Horwood, Chichester, UK 1990). As mentioned hereinabove, using a linear combination of the input variables $E_n$, DFA finds new orthogonal axes (canonical values), in order to minimize the variance within each given class and maximize the variance between two classes. From each group of tested diseases, a defined number of breath samples are randomly chosen and used in order to obtain binary classifiers using DFA. Of the chosen breath samples some are used as training set to obtain the binary classifiers and others are used for blind validation of the acquired classifier. Each of the blind validation samples is classified accordingly, wherein the possible result of said classification test can be True Positive (TP, meaning the subject is afflicted with the tested disease and the classification shows it), False Positive (FP, meaning the subject is not afflicted with the tested disease, but the classification shows he is afflicted), True Negative (TN, meaning the patient is not afflicted with the tested disease and the classification shows it) or False Negative (FN, meaning the subject is afflicted with the tested disease, but the classification does not show it). The classification efficiency is identified by calculating the sensitivity (TP/TP+FN), specificity (TN/TN+FP), and accuracy (TP+TN/sample size) of the constructed model. Each of the test populations afflicted with a particular disease can be analyzed by DFA as compared to the healthy control group. Additionally, the obtained classifiers can be tested to differentiate between two different types of diseases using the selected definitive sensor set. The sensitivity, specificity and accuracy values can be used to evaluate the reliability of the selected database and/or the selected definitive sensor set.

According to some embodiments, the disease-specific pattern is derived from the database by any computational and/or graphical method known in the art. According to some embodiments, the disease-specific pattern is a linear or nonlinear combination of response patterns of the sensor set obtained from the exhaled breath of subjects with a particular disease, present in the database. According to some embodiments, the response patterns to be used for the derivation of a disease-specific pattern are processed by a pattern recognition algorithm, such as, but not limited to, artificial neural networks, principal component analysis (PCA) and discriminant function analysis (DFA) including linear discriminant analysis (LDA). Each possibility represents a separate embodiment of the invention.

According to further embodiments, the method of diagnosing, screening or monitoring a disease provides differentiation between two or more diseases in a subject selected from neurodegenerative diseases, proliferative diseases, inflammatory bowel diseases, respiratory diseases, renal diseases, and obstetric diseases. The method can further provide differentiation between two or more diseases in a subject selected from Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease or pre-eclampsia.

The output signals of the sensor set upon exposure to the breath sample can be detected by a device which measures changes in at least one property of the sensor set, selected from the group consisting of resistance, conductance, alternating current (AC), frequency, capacitance, impedance, inductance, mobility, electrical potential, optical property and voltage threshold. Each possibility represents a separate embodiment of the present invention.

The method of the present invention may comprise the step of concentrating the test exhaled breath sample prior to the measurement using a breath concentrator and/or a dehumidifying unit.

Breath pre-concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., *Anal. Bioanal. Chem.*, 2006, 386, 1059-1073; Coelho et al., *J. Chromatography B*, 2007, 853, 1-9).

II. Sorbent Tubes—Sorbent tubes are typically composed of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than −160° C.) condensation process.

A dehumidifier that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel— is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the larger the amount of water that is adsorbed before equilibrium is reached. Silica gel is advantageous as a drying substance since the process of drying requires no chemical reaction and it produces no by products or side effects.

III. Activated carbon—is formed by processing charcoal to an extremely porous carbon substance. Due to its high degree of microporosity, the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

The method of the present invention enables the detection of a plurality of volatile organic compounds, including the VOCs of the universal biomarker set, which provides differential diagnosis of a plurality of diseases. Said universal biomarker set includes VOCs, which abundance in breath samples of patients with a particular disease was significantly different than the abundance of said VOCs in the breath samples of healthy controls and in breath samples of patients with any other disease.

The term "significantly different" as used herein refers to a quantitative difference in the concentration or level of each VOC from the universal biomarker set in a sample obtained from a patient with a particular disease as compared to the levels of VOCs in control samples obtained from healthy individuals and/or in samples obtained from patients with a different disease. A statistically significant difference can be determined by any test known to the person skilled in the art. Common tests for statistical significance include, among others, t-test, ANOVA1 Kruskal-Wallis, Wilcoxon, Mann-Whitney and odds ratio. Statistical significance may be calculated as $P<0.05$, or more preferably as $P<0.01$. In a further alternative, the significant difference can be determined by recourse to assay reference limits or reference intervals. These can be calculated from intuitive assessment or non-parametric methods. Overall, these methods calculate the 0.025, and 0.975 fractiles as $0.025*(n+1)$ and $0.975*(n+1)$. Such methods are well known in the art. The presence of a VOC biomarker which is absent in a healthy control sample and/or in the different disease sample, is also contemplated as a significant difference. The absence of a VOC biomarker which is present in a healthy control and/or in the different disease sample is also contemplated as a significant difference.

In certain embodiments, universal biomarker set includes 2-ethylhexanol, 3-methylhexane, 5-ethyl-3-methyl-octane, acetone, ethanol, ethyl acetate, ethylbenzene, isononane, isoprene, nonanal, styrene, toluene and undecane.

In some embodiments, the sensor set detects at least 10 of said VOCs from the universal biomarker set. In some embodiments, the sensor set detects at least 11 of said VOCs from the universal biomarker set, or at least 12 VOCs. Each possibility represents a separate embodiment of the invention. In some exemplary embodiments, the sensor set detects each of said VOCs from the universal biomarker set.

The present invention further provides a method of diagnosing, screening and/or monitoring a disease in a subject, comprising determining the levels of the VOCs of the universal biomarker set in the breath sample. The method comprises the steps of collecting a breath sample from the test subject, determining levels of at least 10 VOCs from a universal biomarker set, comprising 2-ethylhexanol, 3-methylhexane, 5-ethyl-3-methyl-octane, acetone, ethanol, ethyl acetate, ethylbenzene, isononane, isoprene, nonanal, styrene, toluene and undecane; comparing the levels of said VOCs from the test breath sample with the reference levels of said VOCs derived from a database of said VOCs detected in exhaled breath of subjects with known diseases, wherein the combination of the reference levels of each of the VOCs of the universal biomarker set is characteristic of a particular disease, selected from the group consisting of neurodegenerative diseases, proliferative diseases, renal diseases, respiratory diseases, inflammatory bowel diseases, and obstetric diseases; and selecting a closest match between the levels of said VOCs from the test breath sample and the combination of the reference levels of the VOCs of the universal biomarker set. In some embodiments, the method comprises determining levels of at least 11 VOCs or at least 12 VOCs from the universal biomarker set of said VOCs from the unique combination. Each possibility represents a separate embodiment of the invention. In some embodiments, the method includes individually determining levels of each VOC.

In some embodiments, the reference levels of the VOCs include mean levels of the VOCs measured in the breath samples of subjects afflicted with a particular disease.

The determination of the level of the volatile organic compounds of the universal biomarker set can be performed, according to the principles of the present invention, by the use of at least one technique including, but not limited to, Gas-Chromatography (GC), GC-lined Mass-Spectrometry (GC-MS), Proton Transfer Reaction Mass-Spectrometry (PTR-MS), Electronic nose device (E-nose), and Quartz Crystal Microbalance (QCM). Each possibility represents a separate embodiment of the invention.

Gas Chromatography (GC) linked to mass spectrometry (MS) is often used to determine the chemical identity and composition of breath VOCs (Miekisch et al. Clinica Chimica Acta, 2004, 347, 25-39). In this set-up, the GC utilizes a capillary column having characteristic dimensions (length, diameter, film thickness) as well as characteristic phase properties. The difference in the chemical properties of different molecules in a mixture allows the separation of the molecules as the sample travels through the column, wherein each molecule has a characteristic time (termed retention time) in which it passes through the column under set conditions. This allows the mass spectrometer to capture, ionize, accelerate, deflect, and detect the ionized molecules separately. The MS signal is obtained by ionization of the molecules or molecular fragments and measurement of their mass to charge ratio by comparing it to a reference collection.

Proton transfer reaction-mass spectrometry (PTR-MS) is reviewed in Lindinger et al., (Int. J. Mass Spectrom. Ion Process, 1998, 173, 191-241) and Lindinger et al., (Adv. Gas Phase Ion Chem., 2001, 4, 191-241). Briefly, PTR-MS measures VOCs that react with $H_3O^+$ ions that are added from an ion source. VOCs with a proton affinity that is larger than that of water (166.5 kcal×mol$^{-1}$) undergo a proton-transfer reaction with the $H_3O^+$ ions as follows: $H_3O^+ + R \rightarrow RH^+ + H_2O$. At the end of the drift tube reactor, a fraction of the ions is sampled by a quadrupole mass spectrometer, which measures the $H_3O^+$ and $RH^+$ ions. The ion signal at a certain mass is linearly dependent on the concentration of the precursor VOC in the sample air. In PTR-MS only the mass of VOCs is determined, causing some ambiguity in the identity of the VOCs. Thus, this technique does not allow a separate detection of different VOCs having the same mass. Further overlap of ion masses is caused by a limited degree of ion fragmentation and ion clustering in the drift tube.

Quartz Crystal Microbalance (QCM) is a piezoelectric-based device which can measure very small mass changes, mostly down to few nanograms Briefly, QCM works by sending an electrical signal through a gold-plated quartz crystal, which causes vibrations in the crystal at a specific resonant frequency measured by the QCM. The resulted frequency shift can be translated to a change in mass on the QCM surface, mostly via using the Sauerbrey equation:

$$\Delta f = \frac{-2 f_0^2}{A\sqrt{\rho_q \mu_q}} \Delta m$$

This equitation is used to correlate changes in the oscillation frequency of a piezoelectric crystal ($\Delta f$) with the mass deposited on it ($\Delta m$). Other parameters which affect the signals are the resonant frequency ($f_0$), the area between electrodes of the piezo-electric crystal (A), density ($\rho_q$) and shear modulus ($\mu_q$) of quartz.

Electronic nose devices perform odor detection through the use of an array of broadly cross-reactive sensors in conjunction with pattern recognition methods, as, for example, the system of the present invention.

According to various embodiments of the invention, the methods of diagnosing a disease in a subject further comprise a step of providing a suitable treatment to said subject, based on the diagnosed disease. The term "treatment", as used herein, refers in some embodiments, to reversing, alleviating, mitigating, inhibiting the progress of, or preventing the disease, disorder or condition to which such term applies or one or more symptoms of such disorder or condition.

For example, physical therapy and/or immunodepressants can be used to treat Multiple Sclerosis. Treatment of Parkinson can include dopamine promoters, antidepressants, cognition-enhancing medication, anti-tremor medications, and their combinations. Cognition enhancing medications can be used for the treatment of Alzheimer disease. If lung cancer is being diagnosed, a suitable treatment may include a surgery, chemotherapy, radiation therapy, targeted drug therapy, immunotherapy, or combinations thereof. Colon cancer can be treated by a surgery, such as, but not limited to, lymph node dissection and colectomy; chemotherapy; and/or radiation therapy. Head and neck cancer treatment can be selected from surgery, including, inter alia, laryngectomy, neck dissection, and flap surgery; radiation, and/or chemotherapy. If ovarian cancer is diagnosed, it can be treated by surgery and/or chemotherapy, wherein the surgery can be selected from omentectomy, laparotomy, hysterectomy, pelvic lymph node dissection, lymph node dissection, salpingoophorectomy, and retroperitoneal lymph node dissection. Typical treatments of bladder cancer include surgery, biological therapy, chemotherapy, ureterostomy, radiation therapy, and urinary diversion. Non-limiting examples of suitable prostate cancer treatments include teletherapy, brachytherapy, particle therapy, radiation therapy, laparoscopic radical prostatectomy, radiosurgery, laparoscopic surgery, prostatectomy, radical retropubic prostatectomy, sex hormone suppression, bone health, chemotherapy, hormone, hormone based chemotherapy, and urinary retention medication. In case of kidney cancer, treatment may include stereotactic radiation therapy, radiofrequency ablation, surgery to remove kidney, chemotherapy and immunotherapy. Some non-limiting examples of treatments suitable for gastric cancer include surgery, such as, gastrectomy and gastroenterostomy, radiation, and/or chemotherapy. The above listed types of cancer treatment may lead to shrinking of tumors, stopping their growth, or slowing down or inhibiting the cell proliferation in the tumors.

For Crohn's disease medications such as steroids and immunosuppressants can be used to slow the progression of disease or a bowel resection can be performed. The non-limiting examples of ulcerative colitis treatments include anti-inflammatory drugs, immunosuppressive drugs, steroid, analgesics, dietary supplements, nonsteroidal anti-Inflammatory drugs, and antibiotics, as well as colostomy, ileostomy, colectomy, and proctocolectomy surgeries. If irritable bowel syndrome is diagnosed in the subject, the treatment step can include administering at least one of diarrhea medication, gut antispasmodic drug, laxative, nerve pain medication, antibiotics, and dietary supplement. In additional embodiments, the treatment of irritable bowel syndrome comprises a therapy selected from biofeedback, cognitive behavioral therapy, and brief psychotherapy. In the case of chronic kidney disease, the treatment step can include medical procedures selected from peritoneal dialysis, hemofiltration, and dialysis; medications including, but not limited to, vitamins, calcium reducers, bone marrow stimulants, diuretics, and dietary supplements; and kidney transplantation surgery.

Pre-eclampsia can often be managed with oral or IV medications until the baby is sufficiently mature to be delivered.

As used herein and in the appended claims the singular forms "a", "an," and "the" include plural references unless the content clearly dictates otherwise. Thus, for example, reference to "an organic coating" or "a disease" includes a plurality of such organic coatings and a plurality of diseases, respectively, and equivalents thereof known to those skilled in the art, and so forth. The term "plurality" means one or more. It should be noted that the term "and" or the term "or" is generally employed in its sense including "and/or" unless the content clearly dictates otherwise. As used herein, the term "about", when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to perform the disclosed methods.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Study Design and Test Population

Breath samples (total number 2808) obtained from 14 departments in nine clinical centers worldwide were subjected to meta-analysis. The same collection equipment and the same strict procedure were used in all participating sites, so the samples were comparable. The clinical features of each examined group are summarized in Table 1.

TABLE 1

Clinical characteristics of all tested patients and controls in the current study

| Group | Diagnosed Subjects | | | | Healthy Subjects | | | |
|---|---|---|---|---|---|---|---|---|
| | n | Age ± SD | Male, n (%) | Smoker, n (%) | n | Age ± SD | Male, n (%) | Smoker, n (%) |
| Lung cancer | 45 | 67 ± 09 | 23 (51%) | 44 (98%) | 23 | 56 ± 14 | 12 (52%) | 12 (52%) |
| Colon cancer | 71 | 66 ± 10 | 42 (59%) | 09 (11%) | 89 | 60 ± 14 | 67 (75%) | 09 (13%) |
| Head & Neck cancer | 22 | 62 ± 12 | 19 (86%) | 13 (59%) | 19 | 50 ± 12 | 06 (32%) | 05 (25%) |
| Ovarian cancer | 48 | 51 ± 11 | 00 (00%) | 00 (00%) | 48 | 47 ± 09 | 00 (00%) | 00 (0%) |
| Bladder cancer | 73 | 69 ± 11 | 68 (93%) | 53 (68%) | 35 | 66 ± 12 | 31 (88%) | 25 (71%) |
| Prostate cancer | 11 | 66 ± 08 | 11 (100%) | 05 (45%) | | | | |
| Kidney cancer | 33 | 65 ± 13 | 22 (66%) | 15 (45%) | | | | |
| Gastric cancer | 99 | 63 ± 12 | 57 (58%) | 26 (27%) | 155 | 57 ± 15 | 55 (34%) | 23 (15%) |
| Crohn's Disease | 41 | 38 ± 12 | 23 (56%) | 20 (50%) | 44 | 41 ± 02 | (28) 60% | 15 (35%) |
| Ulcerative Colitis | 37 | 41 ± 16 | 20 (56%) | 16 (43%) | | | | |
| Irritable bowel syndrome | 27 | 38 ± 13 | 08 (32%) | 08 (30%) | | | | |
| Idiopathic Parkinson | 44 | 65 ± 14 | 23 (53%) | 07 (15%) | 37 | 62 ± 12 | 19 (51%) | 09 (24%) |
| Atypical Parkinsonism | 16 | 67 ± 08 | 07 (44%) | 06 (35%) | | | | |
| Multiple sclerosis | 118 | 38 ± 10 | 42 (36%) | 38 (32%) | 44 | 39 ± 11 | 17 (38%) | 15 (34%) |
| Pulmonary artery hypertension | 22 | 48 ± 12 | 06 (27%) | 12 (54%) | 23 | 38 ± 08 | 10 (43%) | 10 (43%) |
| Pre-eclampsia toxemia | 24 | 30 ± 06 | 00 (00%) | 00 (00%) | 47 | 29 ± 04 | 00 (00%) | 00 (00%) |
| Chronic kidney disease | 82 | 65 ± 12 | 52 (64%) | 24 (29%) | 27 | 46 ± 02 | 12 (45%) | 11 (40%) |
| | 813 | | | | 591 | | | |

The analysis was performed on two breath samples obtained from each of 813 patients diagnosed with one of the following diseases: chronic kidney failure (CKD) (n=82) (Poria Hospital, Tiberias, Israel); idiopathic Parkinson's disease (iPD) and atypical Parkinsonism (PDISM) (n=60) (Carmel Medical Center, Haifa, Israel); multiple sclerosis (MS) (n=118) (Carmel Medical Center, Haifa, Israel); inflammatory bowel disease (IBD), including Crohn's disease (CD) (n=41), ulcerative colitis (UC) (n=37) and irritable bowel syndrome (IBS) (n=27) (Rambam Medical Center, Haifa, Israel); pulmonary arterial hypertension (PAH) (n=22) (French National Referral Center for PAH, Antoine-Béclère Hospital, Paris, France); pre-eclampsia pregnancy in women (PET) (n=24) (Nazareth English Hospital, Nazareth, Israel); head and neck cancer (HNC) (n=22) (Carmel Medical Center, Haifa, Israel); lung cancer (LC) (n=45) (Baptist Cancer Institute (BCI), Jacksonville, Fla., USA); colorectal cancer (CRC) (n=71) (Faculty of Medicine, Riga East University Hospital, Riga, Latvia); bladder cancer (BC) (n=73), kidney cancer (KC) (n=33) and prostate cancer (PC) (n=11) (Bnai-Zion Medical Center, Haifa, Israel); gastric cancer (GC) (n=99) (Faculty of Medicine, Riga East University Hospital, Riga, Latvia); and ovarian cancer (OC) (n=48) (Department of Oncology, First Affiliated Hospital of Anhui Medical University, Hefei, China). The mean age of the patients groups was 55±10 years, 423 (52%) of them were male gender, and included 296 (36%) active smokers. Two breath samples were also collected from each of 591 control subjects enrolled concurrently with the patients at each site. The control population mean age was 52±8 years, 257 (43%) were males, and 134 (23%) were active smokers.

Example 2: Clinical Study

Parkinson Disease (PD)

43 Idiopathic Parkinson's disease, 16 Parkinsonism and 37 healthy subjects were enrolled to the study. The diagnosis of each of the patients was determined according to clinical examination of an experienced specialist. All subjects were above the age of 18 and signed an informed consent. Clinical features of study groups are summarized in Table 2. All Patients were examined at least twice by movement disorders specialist. The first phase included a comprehensive neurological examination for searching clinical signs and symptoms that are indicative to atypical Parkinsonism, including, inter alia: presence of early autonomic signs such as (urinary urgency, impotence and others; recurrent falls in the early stages of the disease progression; cerebral or pyramidal signs; eyes movement disorders (Vertical ophthalmoplegia for instance); past or current psychiatric treatment or the appearance of new psychiatric symptoms or delusions.

In addition, all patients went through Computed Tomography (CT) to rule out other disease(s) such as cancer. Patients suspected with Parkinsonism were examined by Magnetic resonance imaging (MRI) in order to determine the subtype when possible. The last test was responsiveness to L-Dopa treatment, where unresponsive patients were determined when using maximal daily dosage for at least 4 weeks without any signs of response. In both cases, the Mini-Mental Test (MMT), Hoehn and Yahr staging (H&Y) Unified Parkinson's disease Rating Scale (UPRDS) and Schwab & England activities of daily living score were used to determine the severity of the disease and monitoring the progression of the disease.

TABLE 2

Clinical features of the PD study population

| | iPD (n = 43) | Parkinsonism (n = 16) | Healthy (n = 37) | Significance |
|---|---|---|---|---|
| Age - Median (Range) | 67 (22-86) | 66 (47-81) | 62 ± 12 | N.S. |
| Male (%) | 23 (53%) | 7 (44%) | 19 (51%) | N.S. |
| Age at Diagnosis Median (Range) | 62 (19-84) | 64 (47-78) | — | N.S. |
| Disease Duration Median (Range) | 3 (1-15) | 2 (1-8) | — | N.S. |
| L-Dopa treatment (%) | 31 (68%) | 11 (64%) | 0 | N.S. |

TABLE 2-continued

Clinical features of the PD study population

|  | iPD (n = 43) | Parkinsonism (n = 16) | Healthy (n = 37) | Significance |
|---|---|---|---|---|
| Smoker/Past smoker | 7 (15%) | 6 (35%) | 9 (24%) | N.S. |
| MAO inhibitor | 18 (41%) | 0 | 0 | <0.05 |

Multiple Sclerosis (MS)

Breath samples were obtained from 128 MS patients (111 in relapse phase and 17 during Remission) and 47 healthy controls. The sampling took place at Carmel medical center, Haifa, Israel. Clinical features of study groups are summarized in Table 3.

TABLE 3

Clinical features of the MS study population

|  | MS Relapse | MS-Remission | Control |
|---|---|---|---|
| n | 17 | 111 | 44 |
| Age | 37 ± 10 | 39 ± 11 | 39 ± 11 |
| Male | 10 (58%) | 32 (29%) | 17 (38%) |
| EDSS[1] | 4.4 ± 1.4 | 2.8 ± 1.9 |  |
| Diagnosed | 9.9 ± 1 | 12.9 ± 8.6 |  |

[1]Expanded Disability Status Scale

Inclusion Criteria of the MS patients were: relapsing remitting (RRMS) meeting the clinical criteria of McDonald (Polman C H, Reingold S C, Edan G, Filippi M, Hartung H P, Kappos L, et al. Diagnostic criteria for multiple sclerosis: 2005 revisions to the "McDonald Criteria". Ann Neurol. 2005 December; 58(6):840-6) that presented in the MS clinic in Carmel hospital, Haifa Israel. Relapsing MS patients that never received, or have received in the past, or, are currently receiving, or, are about to commence immunomodulatory treatment; MS patients presenting in acute relapse and about to commence a treatment regimen of corticosteroids (IV-Methylprednisolone and oral prednisone); primary progressive (PPMS) meeting the clinical criteria of McDonald that presented in the MS clinic in Carmel hospital, Haifa Israel. Tissue will be collected as previously described; willing and able to give inform consent.

Inclusion Criteria of the MS's Control Group were: age and gender match control individuals that do not have MS or any other condition that is defined as "autoimmune". These individuals were recruited as "Healthy Population Reference" group; willing and able to give informed consent.

Exclusion Criteria: patients age 18 or less, pregnant women; presence of HIV, hepatitis or any other potentially severe and infectious disease. Healthy individual with up to third degree relatives with MS or any other autoimmune diseases.

Inflammatory Bowel Diseases (IBD)

Breath samples were obtained from 41 Crohn's Disease (CR), 37 Ulcerative Colitis (UC), 27 Irritable bowel syndrome (IBS) and 44 healthy controls. All were evaluated by a gastroenterologist and answered a questionnaire. Study subgroups were matched according to age, sex, BMI and smoking status. Clinical features of the study cohort are summarized in Table 4.

All IBD patients older than 18 y/o who agreed to participate in our study were screened. All patients were diagnosed as having CD or UC by an expert gastroenterologist using accepted criteria including clinical presentation, radiologic, endoscopic and histopathological findings. The study included CD patients with ileal involvement only. They completed a physician guided questionnaire, including age, sex, ethnic background, smoking status medical treatment.

All patients over 18 years of age diagnosed with gastrointestinal symptoms that were referred to a gastroenterologist for evaluation were included in the study. Patients who met the Rome Criteria III were screened. Rome Criteria III included suffering from recurrent abdominal pain or discomfort for at least 3 days per month in the last 3 months associated with two or more of the following: 1. Improvement with defecation 2. Onset associated with a change in frequency of stool and 3. Onset associated with a change in form of stool loose or watery stools without pain occurring in at least 75% of stools. All patients had no evidence of an inflammatory, anatomic, metabolic, or neoplastic process that explains their symptoms. They completed a physician guided questionnaire, including age, sex, smoking status and ethnic background.

TABLE 4

Clinical features of the IBD and IBS study population

|  | CD[c] | UC[d] | IBS[e] | Control |
|---|---|---|---|---|
| n | 31 | 28 | 26 | 44 |
| Age | 38 ± 1.9 | 40.5 ± 3 | 38 ± 3 | 41 ± 2 |
| Male (n) % | (n = 18) 56% | (n = 16) 57% | (n = 7) 33% | (n = 28) 60% |
| BMI[a] | 23.9 ± 1.3 | 23.8 ± 0.8 | 23.2 ± 0.9 | 29 ± 1 |
| Current/past smoker | (n = 16) 52% | (n = 10) 36% | (n = 7) 33% | (n = 15) 35% |

The control group included unrelated healthy Israeli volunteers older than 18 y/o randomly recruited from an unselected population. They completed a physician guided questionnaire, including age, sex, smoking status, ethnic background, family history of any gastrointestinal disease and questions that exclude any gastrointestinal symptoms.

Pulmonary Artery Hypertension (PAH)

The diagnosis of PAH was established by means of right heart catheterization and acute vasodilator challenge was performed through inhalation of nitric oxide (NO) or intravenous injection of prostacyclin, according to previously described methods (Sitbon et al., Circulation. 2005 Jun. 14; 111(23):3105-11; Galie et al., Eur Respir J. 2009 December; 34(6):1219-63). Idiopathic PAH (IPAH) was recognized after ruling out all associated conditions summarized in the updated classification (Simonneau et al., J Am Coll Cardiol. 2009 Jun. 30; 54 (Suppl 1):S43-54). Heritable PAH (HPAH) was recognized if a genetic mutation in the genes of the BMP/TGF beta family, including BMPR2, ACVRL1, Endogline, Smad8, was detected and/or if there was more than one confirmed case of PAH in the family even though the mutation was not defined (Sztrymf et al., Am J Respir Crit Care Med. 2008 Jun. 15; 177(12):1377-83).

TABLE 5

Clinical features of the PAH study population

|  | PAH | Controls |
|---|---|---|
| n | 22 | 23 |
| Age (mean ± SD) | 47.5 ± 3.3 | 38.2 ± 2.0 |
| Male (n, %) | 6 (27%) | 10 (43%) |
| Heritable PAH | 15 |  |
| Idiopathic PAH | 7 |  |

TABLE 5-continued

Clinical features of the PAH study population

|  | PAH | Controls |
|---|---|---|
| NYHA (a) functional class | | |
| I & II | 15 | |
| III | 7 | |
| Disease duration | | |
| 0.1-5 years | 9 | |
| >5 years | 13 | |

Twenty one patients out of the 22 were screened for BMPR2 mutations. Seven patients had heritable PAH (6 carriers of a BMPR2 mutation and 1 patient with a confirmed family history of PAH but no mutation identified in known PAH predisposing genes) and 15 patients had idiopathic PAH (14 screened for BMPR2 mutations and non-carriers). Five patients acutely responded to vasodilators and were treated by calcium channel blockers. The other patients received conventional mono or combined therapy for PAH. Patients with HPAH, carrying a BMPR2 mutation, had similar therapy as the IPAH patients. All patients under prostanoids received either intra-venous or sub-cutaneous treatment; none of the patients included were on inhaled prostanoids. Clinical features of study groups are summarized in Table 5.

Chronic Kidney Disease (CKD)

Breath samples were obtained from 82 CKD patients with different severity levels, and 27 healthy controls. The samples were collected in a controlled manner as described previously. Each of the patients went through a comprehensive physical examination, as well as, blood and urine routine tests. None of the patients had dialysis or renal transplantation at the time of the breath testing. The biochemical data were obtained from standard blood tests less than 1 month prior to the breath testing. The patients were staged according to the estimated GFR (eGFR) that was calculated from the plasma creatinine levels, patient age and gender, using the modification of diet in renal disease equation. 27 patents were considered as early stage CKD (stage 1 and 2) while 49 were determined as advanced stage (stages 3-5). The staging of 6 patients was not definite and therefore was excluded in part of the analysis. The clinical features of the cohort sample are summarized in Table 6.

TABLE 6

Clinical features of the CKD study population

|  | CKD | Early stage | Late stage | Controls |
|---|---|---|---|---|
| n | 82 | 27 | 49 | 27 |
| Age | 65 ± 12 | 60 ± 6 | 67 ± 1 | 46 ± 2 |
| Male % | 64% | 55% | 70% | 45% |
| GFR[a] | 51 ± 3.5 | 89.4 ± 4.2 | 32.8 ± 2.1 | NA |
| Creatinine (mg/dl) | 1.8 ± .13 | 0.83 ± 0.03 | 2.3 ± 0.1 | 0.68 ± 0.01 |
| BUN[b] (mg/dl) | 40.9 ± 2.9 | 15.4 ± 1 | 49.7 ± 3.6 | 12.6 ± .5 |
| Urea (mg/dl) | 99.1 ± 29.4 | 35 ± 2.3 | 128 ± 45 | NA |

[a]Glomerular Filtration Rate
[b]Blood Urea Nitrogen

Pre-Eclampsia Toxemia (TOX)

92 Breath samples were collected in controlled manner both in the English Hospital in Nazareth (Israel) and the Ha'Emek Medical Center in Afula (Israel). The study cohort consisted of 3 groups of women, as described in Table 7. The main groups were divided as follows:
1. Pre-Eclampsia Toxemia (PET): 31 pregnant women after the 24$^{th}$ week of pregnancy with life fetus. PET was diagnosed according to the American College of Obstetricians and Gynecologists (ACOG) criteria (Blood pressure higher than 140/90 and Proteinuria).
2. Healthy Pregnant (HPR): 31 healthy pregnant women after the 24$^{th}$ week of pregnancy, without a history of any chronic diseases and/or pregnancy complications.
3. Not-Pregnant Controls (CNP): 30 non-pregnant, without history of medical disease and or treatments.

The Exclusion Criteria included: Age under 18, Pre-Pregnancy Body Mass Index >35, Cigarette smoking and Chronic diseases and/or treatments.

TABLE 7

Clinical features of the Toxemia and pregnant women study population

|  | Preeclampsia Toxemia | Healthy Pregnant | Non pregnant Controls |
|---|---|---|---|
| n | 24 | 26 | 21 |
| Age | 30 ± 5.6 | 27.3 ± 0.7 | 29.3 ± 1 |
| Age of pregnancy (weeks) | 34.7 ± 3.1 | 32.3 ± 3.9 | — |
| BMI (before pregnancy) | 26.8 ± 4.5 | 23.2 ± 5 | 23.1 ± 3 |
| Current BMI | 31.6 ± 7.8 | 26.8 ± 4.8 | — |
| Proteinuria | 733 ± 155 | | — |

Gastric Cancer (GC)

Patients with GC (morphologically confirmed adenocarcinomas) were enrolled prior to surgery. No chemotherapy or radiation therapy was allowed prior to the enrolment. Patients with non-malignant diseases were enrolled prior to upper endoscopy. Patients having an old scar or deformation of the gastro-duodenal zone without the evidence of fresh ulceration were not included to the groups.

Five biopsies corresponding updated Sydney system were obtained and stained with haematoxylin and eosin and Giemsa stains as a routine. Operative link on gastric intestinal metaplasia (OLGIM) assessment staging system was used to stratify the presence/absence and risk level of the premalignant lesions (PMLs) (13). The staging system is considering the presence and stage of IM in the corpus and antral part of the stomach (incisura biopsy is analysed together with antral biopsies). OLGIM 0 characterizes gastric mucosa with no IM. Histology confirmation of all the diagnosis was required. The pathology slides were read and confirmed by expert pathologists.

Patients having undergone stomach surgery in the past were excluded from the study. Current smokers were included to the groups of "smoking" individuals.

Ovarian Cancer (OC)

All breath samples were recruited from the First Affiliated Hospital of Anhui Medical University, Hefei, China; the Anhui Province Hospital and the Maternal and Child Health Hospital of Anhui Medical University. The subjects (all female) had not ingested food, coffee and alcohol for 2 hours before the sampling. The subjects were instructed to waive all kinds of cosmetic and perfume during the day of the breath collection. The details of the subjects examined are shown in Table 1. As seen in the table, the subjects were divided into two main groups. The first group consisted of 48 cases of OC (Malignant ovarian neoplasia) divided as follows: 40 cases with epithelial ovarian cancer origin (EOC), known as "true ovarian carcinoma"; 2 cases of germ cells origin; and 6 cases of borderline ovarian tumor. Twenty-five cases were classified as early stage (I and II stage) and 22 cases were classified as advanced stage (III and IV). The stage of one case is unknown. The clinical stage of the OC was determined according to the American Joint Committee on Cancer Staging and the International Federation of Gynecology and Obstetrics. The cancer conditions in all examined patients were determined by pathology. The second group consisted of 48 tumor free (TF) control females. The TF volunteers were recruited among the patients' relatives and the hospital staff. None of the participants of this study had a history of cancer or other chronic disease such as hypertension, diabetes, autoimmune diseases (such as rheumatoid arthritis or systemic lupus erythematosus). All volunteers were nonsmokers and pregnancy was an exclusion criterion in all examined groups.

Head and Neck Cancer (HNC)

Breath samples were collected at the Otolaryngology Head and Neck Department, Carmel Medical Center, Haifa, Israel, from 44 female and male volunteers after obtaining written informed consent. The 19 healthy controls were recruited among the patients' accompanying persons, usually their spouses, in order to match them to the patients with regard to age and lifestyle. In this way, however, the control and patients groups could not be gender-matched, because malignant lesions of the head and neck occur predominantly in men. The healthy volunteers were not aware of any disease state and did not undergo medical examination. The following exclusion criteria were applied to all 42 volunteers before sample collection: past medical history of any malignancy as well as any former oncological treatment, age under 18, an active infectious disease, present antibiotic treatment, pregnancy or lactation. The 22 malignant patients underwent pertinent anamnesis, physical examination and radiological studies when indicated, in view of the different lesions. Flexible nasolaryngoscopy was a mandatory step in the preliminary assessment. Biopsies were then taken from all 22 participating patients for tissue diagnosis. Breath samples were collected before taking biopsies; enrollment in the study did not delay the biopsy or interfere with the management protocol in any case. Oropharyngeal malignant lesions were assessed for Human Papilloma Virus (HPV) status by immunohistochemistry and all samples were HPV negative.

Hence, for this study the samples of 42 well defined subjects were analyzed: 22 with squamous cell carcinoma of the head and neck (HNSCC) (site: larynx and pharynx), and 19 healthy controls.

HNC is classified according to primary tumor stage (T), regional lymph node stage (N) and distant metastasis stage (M). The 22 HNSCC patients in this study included 9 patients with early stage disease (T≤2; N=0; M=0), 11 patients with late-stage disease (all higher TNM classifications) and two patients were not staged.

Ethical approval has been obtained from the institutional review board of Carmel Medical Center, and the study has been registered at http://clinicaltrials.gov. The treatment decisions were based solely on the conventional diagnosis described above.

Colorectal Cancer

Patients referred for either surgery or diagnostic colonoscopy in Riga East University hospital or Digestive Diseases Centre GASTRO were recruited to the study group. Breath samples were collected prior to potential removal of any lesions, i.e. prior to surgery or colonoscopy. The samples for volatile marker testing were collected after an overnight fast and after withholding from smoking for at least 2 hours. Patients with any active other malignancy at the time sampling as well as those having undergone major gastrointestinal surgery in the past were not recruited. Patients with IBD (either diagnosed or suspected disease) were also excluded. The clinical features of the cohort sample are summarized in Table 8.

TABLE 8

Clinical features of the colon cancer study population

|  | Colorectal Cancer | Control |
| --- | --- | --- |
| n | 71 | 89 |
| Age ± SD | 66 ± 10 | 60 ± 14 |
| Male, n (%) | 42 (59%) | 67 (75%) |
| Smoker, n (%) | 9 (11%) | 09 (13%) |

Bladder, Kidney and Prostate Cancers

Breath samples were obtained from patients admitted to the department of urology, Bnai Zion Medical Center, Haifa Israel. All patients were instructed to fast for at least 12 hours before the test. The study population included 152 patients divided into four groups: Group I consisted of 73 patients with bladder lesions. The Second group consisted of 33 patients with enhancing solid renal masses of malignant kidney cancer. The Third group consisted of 11 patients with localized prostate cancer. The fourth group consisted of 35 participants, this group went through a series of imaging tests of the urinary tract that ruled out malignancy and served as a control group. The diagnosis of malignancy and histological grade was based on standard pathology of the relevant specimen. Disease stage was determined based on imaging studies including ultrasound, computed tomography or magnetic resonance imaging. None of the patients had another genitourinary malignancy or have received prior anti-cancer treatment. The study was approved by the hospital ethical committee and all participant signed a written informed consent before the test was collected. Clinical features of these four groups are summarized in Table 9.

TABLE 9

Clinical features of the bladder, kidney and prostate cancer study population

|  | Bladder Cancer | Kidney Cancer | Prostate Cancer | Controls |
| --- | --- | --- | --- | --- |
| n | 73 | 33 | 11 | 35 |
| Age | 69 ± 11 | 65 ± 13 | 66 ± 08 | 66 ± 12 |
| Male | 68 (93%) | 22 (66%) | 11 (100%) | 31 (88%) |
| Current/past smokers | 53 (68%) | 15 (45%) | 05 (45%) | 25 (71%) |

Lung Cancer (LC)

Fifty three newly diagnosed LC patients, with various histology abnormalities and stages, were recruited between February 2012 and June 2013 and registered at the Baptist Cancer Institute (BCI), Jacksonville, Fla., USA. All patients had histologic confirmation of malignancy, and diagnosis was made via bronchoscopic brushings, washings, or biopsies (34), CT directed needle biopsies (17), sputum cytology (1), or open biopsy (1). Eligible patients had pathologic cancer confirmation, no prior cancer history, and had not yet started any cancer therapy for their primary lung tumor. 3 patients were excluded either because they withdrew consent prior to testing or due to other technical difficulties. All 50 remaining patients completed detailed personal medical histories and underwent 5 early detection tests: a PET/CT scan, a breath analysis, serum tumor autoantibody assay, serum protein tumor marker assay, and 3D cell-CT sputum cytology analysis. There were no dietary or lifestyle restrictions on the patients prior to or during testing. Most were current or prior smokers and most had one or more co-morbid illnesses. A variety of histologies were seen (Small Cell Lung Cancer-8, Adenocarcinoma-26, squamous cell carcinoma-14, non-specified non-small cell-1, and carcinoid-1). Simultaneously, 23 control patients with benign pulmonary disease (COPD/asthma-14, dyspnea-4, cough-2, abnormal chest x-ray-2, and sarcoidosis-1) were asked to provide breath samples for calibration purposes. Fifteen patients had early stage disease (I/II), and 35 were advanced (III/IV). The breath samples of 5 patients were excluded due to technical difficulties during analysis (n=45). Clinical features of these four groups are summarized in Table 10.

TABLE 10

Clinical features of the lung cancer study population

|  | Lung Cancer | Controls |
|---|---|---|
| n | 45 | 23 |
| Age (mean ± SD) | 62 ± 12 | 56 ± 14 |
| Male (n, %) | 19 (86%) | 12 (52%) |
| Current/Past Smoking | 13 (59%) | 12 (52%) |
| FEV1$^a$ (Liter) | 1.79 | — |

$^a$Forced Exhaled Volume 1$^{st}$ second

Example 3: Breath Sample Collection

All breath samples were collected in a controlled manner following a strict protocol. The same breath collection equipment and procedure was applied in all breath collection locations. The breath collection procedure started with a 3-5 minutes "lung wash". During this process, the subject inhales via both a charcoal (ABEK) and bacterial filter, cleaning about 99.99% of the exogenous VOCs found in ambient air. When done, the subject exhaled through the device, which has two separate ports. One port directs the first part of the exhaled air, consisting mainly of dead space air, to a plastic bag. The rest of the exhaled air (the alveolar air) is directed to a 750 ml chemically inert Mylar sampling bag. The process was repeated after a short period, for a total of two samples for each subject. By the end of the sampling process, the content of each Mylar bag was transferred, using a simple vacuum air pump, into a Tenax TA and Carboxen-1018 glass adsorbent tube (Sigma Aldrich Ltd.) or into in two-bed ORBO™ 420 Tenax TA sorption tubes (Sigma-Aldrich, St Louis, Mo., USA). For the sake of quality control, the room air samples were collected by pumping ambient air in the collection room through a sorbent tube for 7 min at a rate of 150 ml/min. The tubes were sealed and stored in 4° C. refrigerators until analysis. One sample was used for chemical analysis using GC-MS and the other for sensor array pattern recognition analysis. It is important to emphasize in this context that ambient air samples were collected in each location, during each sampling day.

All samples were analyzed by two independent approaches. The first approach is based on chemical analysis by gas chromatography linked with mass spectrometry (GC-MS) for the identification and quantification of the variety of breath VOCs exist in each studied group, as detailed in Example 4, hereinbelow. The second method is based on cross-reactive nanoarray sensors in combination with pattern recognition methods, as detailed in Example 5, hereinbelow. This approach provides collective VOC patterns rather than specific VOC identification and quantification.

TABLE 11

Breath collection locations and disease samples

| Location | Disease states | Sick | Control | Breath Kit used |
|---|---|---|---|---|
| Poria Hospital, Tiberias | Chronic Kidney Failure | 82 | 25 | Reusable |
| Rambam medical center, Haifa | Crohn's Disease Ulcerative Colitis Irritable bowel syndrome | 123 | 47 | Reusable |
| Antoine-Beclere Hospital, Paris, France | Pulmonary artery Hypertension | 22 | 23 | Reusable |
| Nazareth English Hospital, Nazareth | Pre-Eclampsia Toxemia | 24 | 50 | Reusable |
| Carmel Medical Center, Haifa, Israel | Idiopathic Parkinson's Atypical Parkinsonism | 60 | 37 | Disposable |
| Carmel Medical Center, Haifa, Israel | Multiple Sclerosis | 118 | 50 | Disposable |
| Carmel Medical Center, Haifa, Israel | Head and Neck Cancer | 22 | 20 | Disposable |
|  | Lung cancer | 45 | 22 |  |
| Department of Oncology, the First Affiliated Hospital of Anhui Medical University, Hefei, China. | Ovarian Cancer | 48 | 48 | Disposable |
| Department of Research, Riga East University Hospital, Riga, Latvia | Colon Cancer | 72 | 89 | Disposable |
| Bnai-Zion medical center, Haifa, Israel | Kidney | 33 | 37 | Disposable |
| Bnai-Zion medical center, Haifa, Israel | Bladder | 73 |  |  |

TABLE 11-continued

Breath collection locations and disease samples

| Location | Disease states | Sick | Control | Breath Kit used |
|---|---|---|---|---|
| Bnai-Zion medical center, Haifa, Israel | Prostate | 11 | | |
| Department of Research, Riga East University Hospital, Riga, Latvia | Gastric Cancer | 99 | 155 | Disposable |
| Total | | 832 | 603 | 1435 |

Example 4: GC-MS Analysis of the Breath Samples

To explore the nature of the breath composition, one breath sample obtained from each of the 1404 subjects was analyzed by GC-MS, using the same instrument and fixed analysis conditions for all samples.

The GC-MS analysis was divided into two steps. In the first step, the sample went through the GC capillary column, in which the velocity of a molecule is correlated to its chemical properties; hence, different molecules exit the column in varying time point (retention time). The separation of the mixture allows the MS to capture, ionize, accelerate, deflect, and detect the ionized molecules separately. The MS does this by breaking each molecule into ionized fragments and detecting these fragments using their mass to charge ratio and comparing it to a given library. The final output contains a Chromatogram, which the retention time to the abundance of each of the compound. The area under curve, for a specific compound, is proportional to its concentration in the mixture. One of the two breath samples, obtained from each volunteer, was analyzed using GC-MS, to determine the chemical nature and composition of his/her exhaled breath. For this analysis, GC-MS (GCMS-QP2010; Shimadzu Corporation, Japan), combined with a thermal desorption system (TD20; Shimadzu Corporation, Japan), was used. The following oven temperature profile was set: (a) 10 min at 35° C.; (b) 4° C./min ramp until 150° C.; (c) 10° C./min ramp until 300° C.; and (d) 5 min at 300° C. An SLB-5 ms capillary column (Sigma Aldrich Ltd.) with 5% phenyl methyl siloxane (30 m length, 0.25 mm internal diameter, and 0.5 μm thickness) was employed. The splitless injection mode was used for 2 min, at 30 cm/s constant linear speed and 0.70 mL/min column flow. Prior to analysis, the tubes were conjugated to a 30 ml/min flow of pure helium, to reduce the amount of humidity accumulated in them. GC-MS chromatogram analysis was realized using the GC-MS solutions version 2.53SU1 Postrunanalysis program (Shimadzu Corporation).

Owing to the differences in demographic characteristics of the populations for each disease, statistical methods were used to test for and eliminate possible confounding effects. Multiple linear regression models were applied to the GC-MS outcomes to examine the association between the dependent variable (area under peak of each identified VOC) and the independent variables (age, sex, location and smoking status). Linear adjustments were then made for covariates presenting significant correlations (P value <0.05), and the multiple linear regression was applied again to the corrected data to verify the correction (disappearance of statistical significance). Student's t-test and/or non-parametric Wilcoxon tests were used to determine statistical differences in VOC abundances among the study groups. Due to major technical difficulties and repair of the instrument, the breath samples collected from CKD patients were analyzed in a different manner and technical parameters, than the rest of the study cohort, and therefore, were excluded from the GC-MS analysis.

Results

Over 150 different VOCs were identified in the different cohorts. However, the inventors of the present invention focused on 35 that: (i) were common to more than 70% of the total study population (patients and controls); (ii) were easily identified and verified by the analysis of pure standards; and (iii) had concentrations in ambient air samples at least 10-fold lower (in average) than in the equivalent breath samples. Owing to the demographic differences among the study groups, a multiple linear regression was first performed for the abundance of each of the 35 VOCs, exploring any correlation between abundance and the covariates (age, sex, location and smoking status). The results indicate that the abundances of 15 VOCs were negatively correlated with age and/or smoking. Three of them were also correlated with gender. However, no significant correlation was found between the abundance of any VOC and the site of sampling. Therefore, each VOC presenting significant correlations (p-value <0.05) was adjusted according to the calculated coefficient corresponding to the confounding element (Table 12).

TABLE 12

Effect of confounding factors on the tested volatolome.

| | Significant correlation (P value < 0.05) | | | |
|---|---|---|---|---|
| VOC | Age | Smoking | Gender | Location |
| 2-ethylhexanol | x | x | | |
| 3-methylhexane | | x | | |
| 5-ethyl-3-methyl-octane | x | | | |
| Acetone | x | | | |
| Ethanol | x | x | | |
| Ethyl acetate | x | x | | |
| Ethylbenzene | x | | | |
| Isononane | x | | x | |
| Isoprene | x | | | |
| Nonanal | x | | x | |
| Styrene | x | | | |
| Toluene | x | | | |
| Undecane | x | x | x | |

Table 12 summarizes the multilinear regression models applied on the concentrations of the reported VOC. Significant correlation between the VOCs concentrations and independent variables including Age, Smoking habits, Gender and sampling site are indicated in the following table. The concentration of each of VOCs was then corrected according to the linear coefficient associated with the correlation.

The statistical analysis revealed that no single VOC could discriminate a specific disease from the related control group. Moreover, no single VOC was sufficiently statistically informative to discriminate among different types of diseases. Rather, 13 different VOCs common to all examined diseases in the current study were observed that differed significantly (P-value <0.01) in abundance from the control groups and/or from the other diseases. These 13 VOCs were: 2-ethylhexanol, 3-methylhexane, 5-ethyl-3-methyl-octane, acetone, ethanol, ethyl acetate, ethylbenzene, isononane, isoprene, nonanal, styrene, toluene and undecane (Table 13).

TABLE 13

Characteristics of the statistically validated VOCs

| VOC | Main M/z | Ret. Time | Cas number |
|---|---|---|---|
| 2-ethylhexanol | 57 | 29.3 | 104-76-7 |
| 3-methylhexane | 43 | 6.5 | 589-34-4 |
| 5-ethyl-3-methyl-octane | 43 | 28.7 | 62016-21-1 |
| acetone | 43 | 2.75 | 67-64-1 |
| ethanol | 31 | 2.5 | 64-17-5 |
| ethyl acetate | 43 | 4.4 | 141-78-6 |
| ethylbenzene | 91 | 18.5 | 100-41-4 |
| isononane | 43 | 18.8 | 3221-61-2 |
| isoprene | 67 | 2.9 | 78-79-5 |
| nonanal | 57 | 30.5 | 124-19-6 |
| styrene | 104 | 20.5 | 100-42-5 |
| toluene | 91 | 12.5 | 108-88-3 |
| undecane | 43 | 25.8 | 1120-21-4 |

Figure 1B:
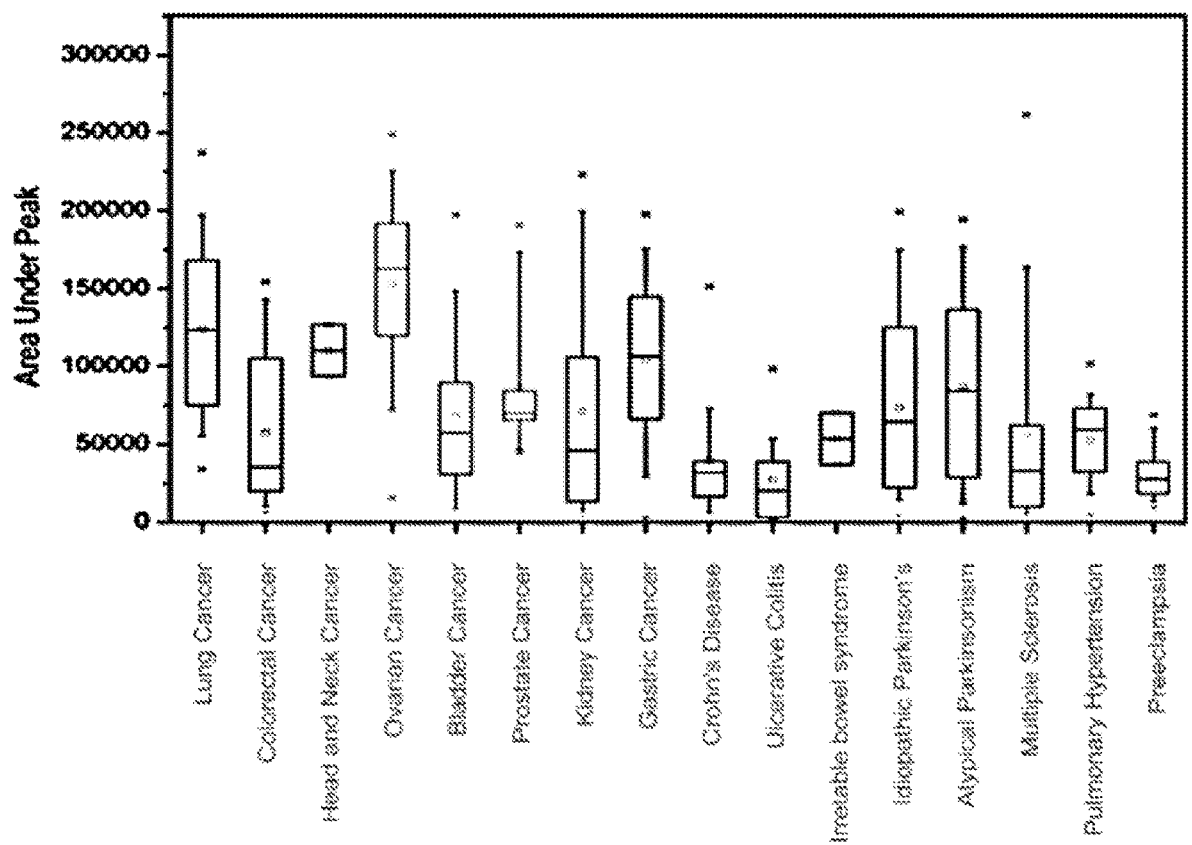
Figure 1C:
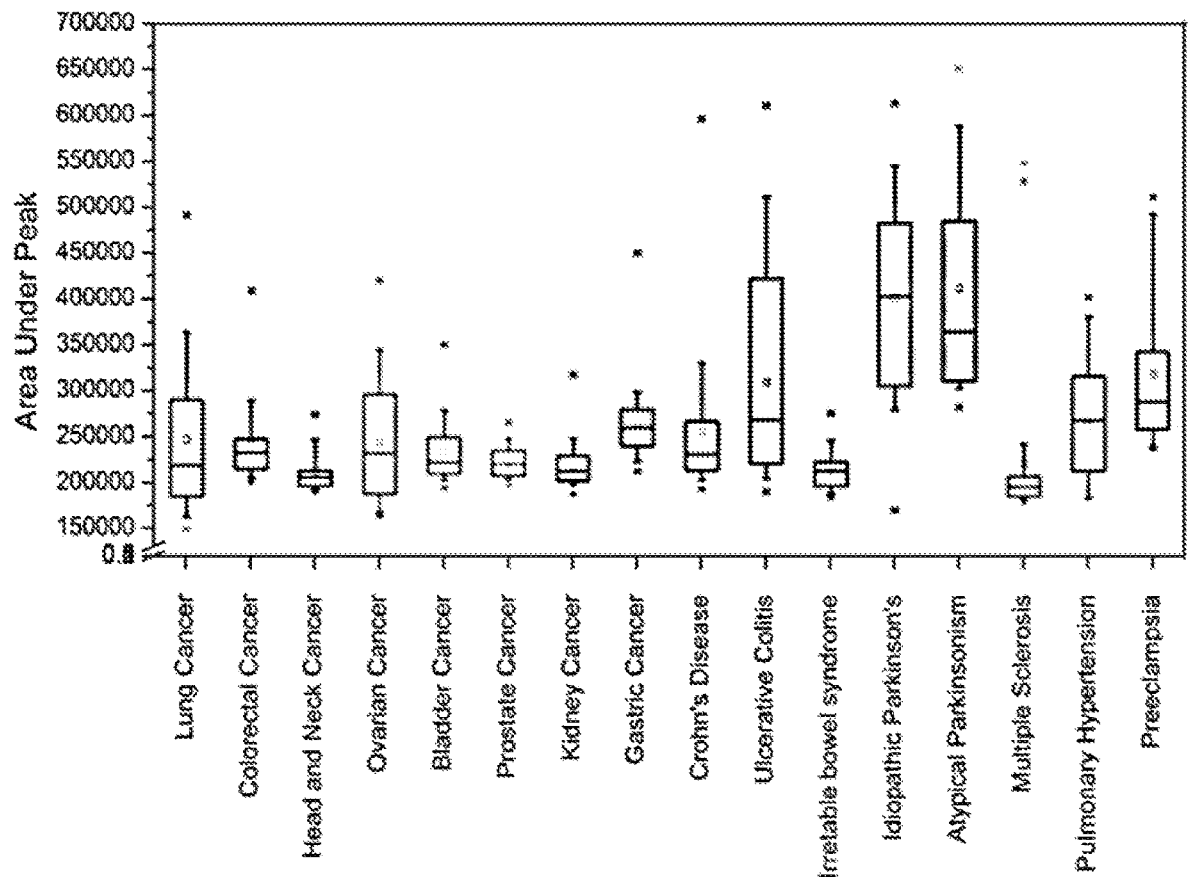
Figure 2A:
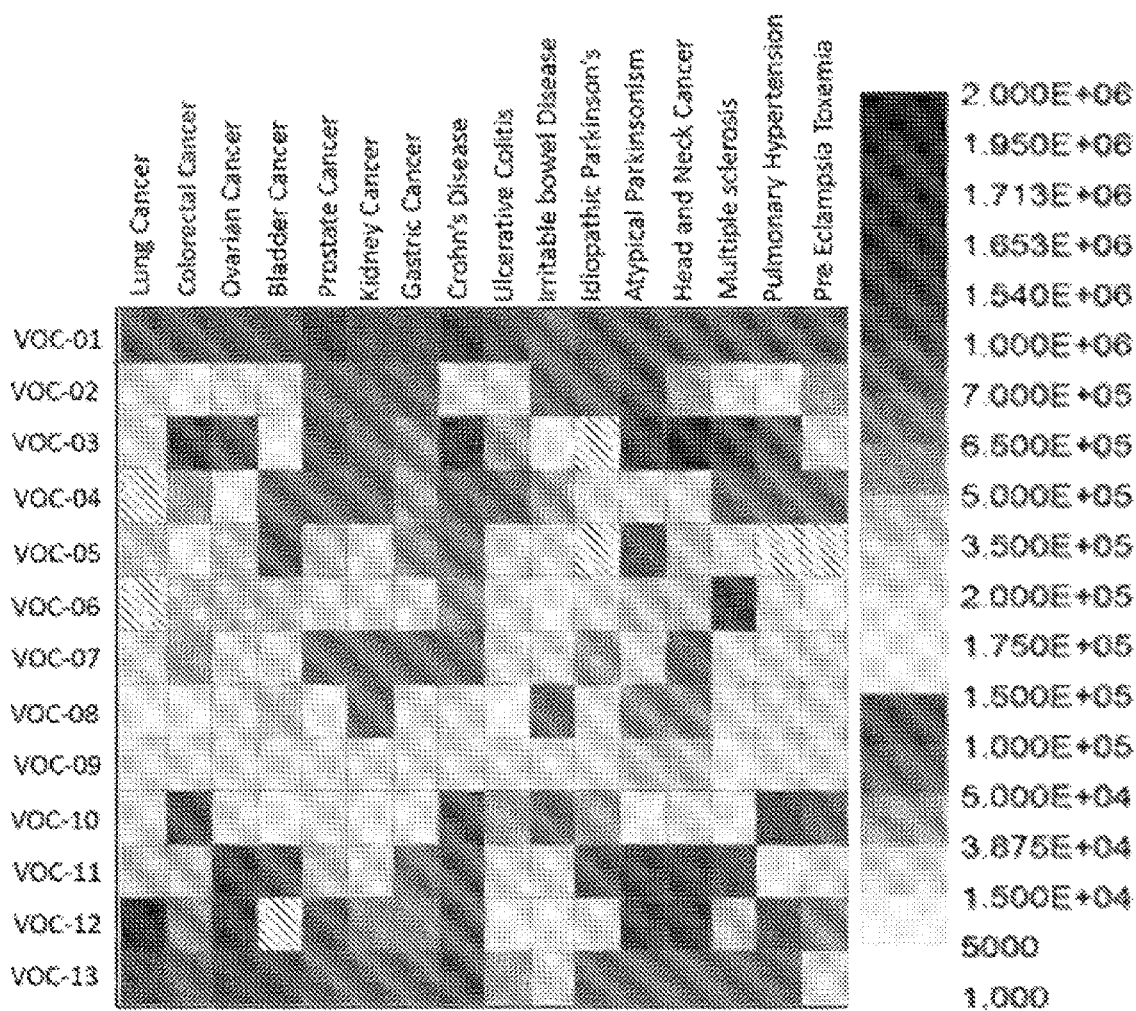
FIG. 2A: Heat map (in black and white) of the quantitative GC-MS analysis of the patients' breath samples. The average of each of the 13 VOCs is presented on the color-scale. Boxes with slashes represent cases in which the VOC was found in less than 70% of the samples of a specific group of patients. The VOCs are 2-ethylhexanol, 3-methylhexane, 5-ethyl-3-methyl-octane, acetone, ethanol, ethyl acetate, ethylbenzene, isononane, isoprene, nonanal styrene, toluene and undecane (numbered respectively).

The breath volatolome of each examined group, i.e., the combination of the 13 statistically-validated VOCs, showed clear differences among the diseases. Although the abundances of these VOCs overlapped among some of the disease states, significant differences was clear among others. For example, nonanal was significantly lower in Crohn's disease, irritable bowel syndrome and preeclampsia than other diseases (FIG. 1A). Undecane was dramatically higher in lung cancer, head and neck cancer and ovarian cancer than the remaining groups. It was also significantly lower in Crohn's disease, ulcerative colitis and pulmonary hypertension than the remaining groups (FIG. 1B). Isononane, in contrast, was significantly higher among patients with idiopathic Parkinson's disease, atypical Parkinsonism and preeclampsia than all other diseases (FIG. 1C). A similar pattern was evident for each of the other 10 VOCs. As seen in the color-map in FIG. 2A, it is almost impossible to discriminate between the different diseases at the single VOC level (rows in the heat map). However, the overall combination of 13 VOCs (columns in the color-map) obtained for a specific disease differs from the other diseases. In other words, the results in FIG. 2A show a clearly distinct breath volatolomic signature for each disease.

Figure 2B:
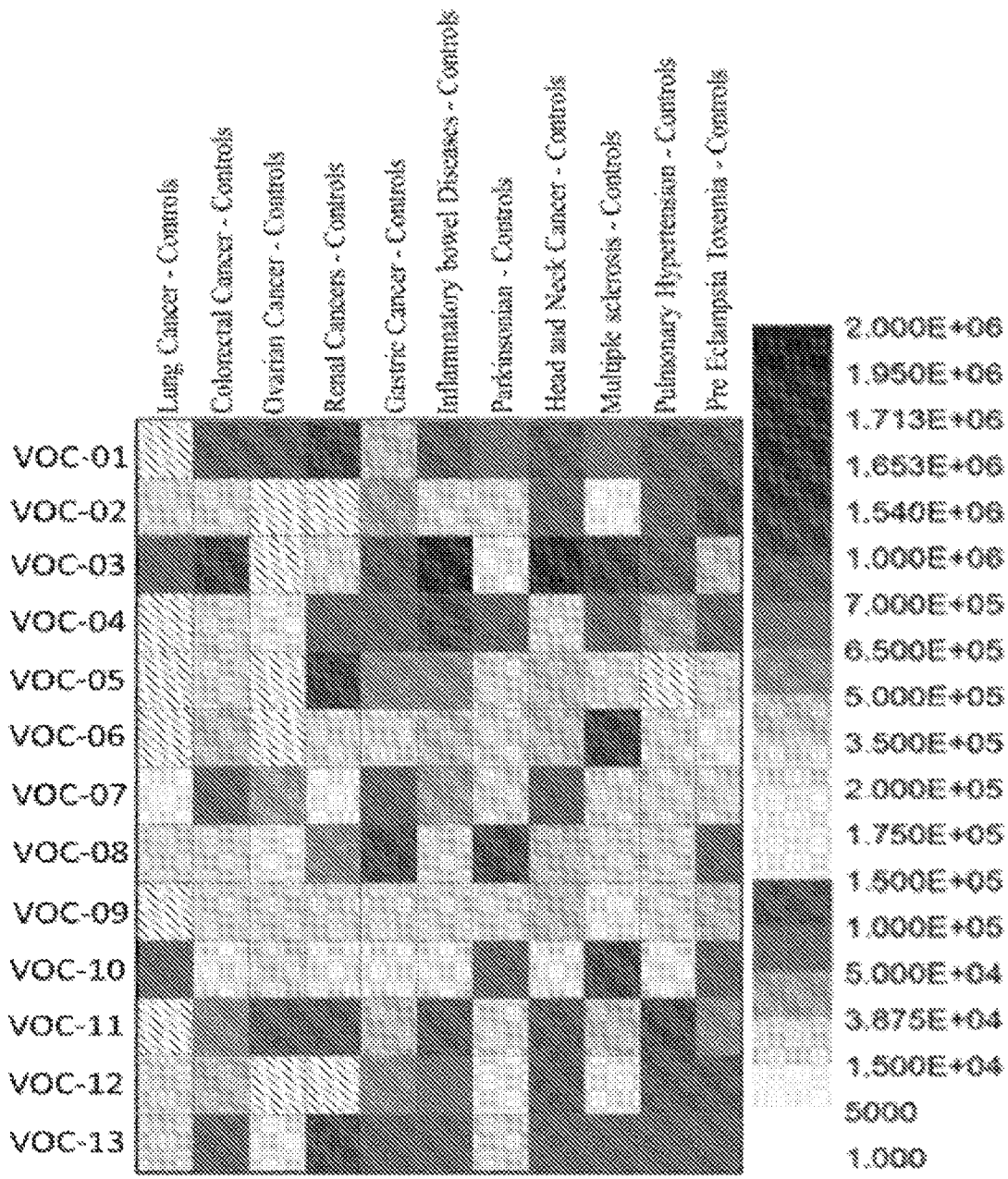
FIG. 2B: Heat map (in black and white) of the quantitative GC-MS analysis of the control breath samples. The average Area under Peak of each of the 13 VOC is presented according to the color-scale. Boxes with slashes represents cases in which the VOC was found in less than 70% of the samples of a specific group of controls. The VOCs are numbered as in FIG. 2A.

Examining the aforementioned 13 VOCs in the various control groups (FIG. 2B) showed that the number of cases with significant differences in VOC abundances among these groups (P-value <0.01) was 35% lower. In fact, there were significant differences (P-value <0.01) in 177 of the 858 (i.e., 21%) binary comparisons among the control groups collected concomitantly with the disease groups. For comparison, there were significant differences (P-value <0.01) in 760 of the 1768 (i.e., 43%) of the binary comparisons between the various disease groups. This demonstrates intra-individual differences in the breath volatolomes of the controls, but much more obvious and remarkable ones among patients with different diseases.

Regression models applied to the raw GC-MS data from 1404 breath samples revealed that breath volatolomics are affected by common confounding factors. Although the overall volatolome composition was preserved, concentrations of a wide range of VOCs were affected by age and/or smoking habits, while fewer were correlated with the genders of the tested subjects. Anatomical and physiological changes in the respiratory system and circulation, associated with aging and/or smoking injury, are well known. This includes stiffness and degeneration of the elastic fibers, fibrosis, aging-associated destruction of lung parenchyma, emphysema and chronic bronchitis, mainly among smokers. Such alterations could easily affect the diffusion of VOCs through the blood-air barrier by altering the layer thickness or permeability (so-called membrane conductance) or by reducing the total surface area of the membrane. These factors could easily alter the flux, according to Fick's first law, affecting the diffusion of gases in the exhaled air, eventually reducing/stressing the expression and/or concentrations of wide range of the exhaled volatolome components. On the other hand, only three VOCs were correlated with gender.

Taking the confounding factors and regression results into account, as described above, none of the VOCs was informative enough to be used as a threshold-based biomarker for any particular disease or group of related diseases (e.g. cancerous vs. non-cancerous) and/or population-related characteristics (geographic/ethnic etc.). Rather, it was noticed that the same VOCs are altered in more than one disease state, indicating that different pathophysiological pathways could affect a variety of VOCs and that specific VOCs could be influenced by multiple pathways. In other words, the results indicate that the breath volatolome is produced continually by many physiological systems. However, during the course of disease, the balance between production rates might be altered in specific pathways, leading to overall changes in the breath volatolome.

Without wishing to being bound by theory or mechanism of action, it is contemplated that the results of this study indicate that despite the intra-individual volatolomic differences, each disease has a remarkably distinctive volatolome composition that differentiates it from both controls and other disease states; furthermore, the collective volatolome is more informative than any specific VOC.

The VOCs obtained in this study are well known and documented in the literature, and each single VOC was obtained in various disease states. For example, nonanal was linked to ovarian cancer [Amal H, et al. Assessment of ovarian cancer conditions from exhaled breath. *International Journal of Cancer*, 136(6), E614-E622 (2015)], inflammatory bowel disease [Hicks L C, et al. Analysis of Exhaled Breath Volatile Organic Compounds in Inflammatory Bowel Disease: A Pilot Study. *J Crohns Colitis* 9, 731-737 (2015)], breast cancer [Li J, et al. Investigation of potential breath biomarkers for the early diagnosis of breast cancer using gas chromatography-mass spectrometry. *Clin Chim Acta* 436, 59-67 (2014)] and esophageal and gastric adenocarcinoma [Kumar S, et al. Mass Spectrometric Analysis of Exhaled Breath for the Identification of Volatile Organic Compound Biomarkers in Esophageal and Gastric Adenocarcinoma. *Ann Surg* 262, 981-990 (2015)]. As another example, isoprene was linked to chronic liver disease [Alkhouri N, et al. Isoprene in the Exhaled Breath is a Novel Biomarker for Advanced Fibrosis in Patients with Chronic Liver Disease: A Pilot Study. *Clin Transl Gastroenterol* 17, 40 (2015)], kidney diseases [Davies S J, Spanel P, Smith D. Breath analysis of ammonia, volatile organic compounds and deuterated water vapor in chronic kidney disease and during dialysis. *Bioanalysis* 6, 843-857 (2014)], diabetes [Smith D, Spanel P, Fryer A A, Hanna F, Ferns G A. Can volatile compounds in exhaled breath be used to monitor control in diabetes mellitus? *J Breath Res* 5, 1752-7155 (2011)] and others. However, none of said previously reported results suggests a collective VOC pattern which can be used to discriminate among different diseases.

Example 5: Fabrication of Sensors

The second of the two breath samples, obtained from each volunteer, was introduced via an exposure cell and analyzed by an array of cross-reactive sensors that relates to two main chemiresistive categories: (i) monolayer-capped gold nanoparticles (core diameter: 3-4 nm); and (ii) organically functionalized random network of single-walled carbon nanotubes (SWCNTs).

Gold nanoparticles were synthesized as described in Dovgolevsky et al., J PHYS CHEM C. 2010 2010/08/26; 114:14042-9; Dovgolevsky et al., Small 2009; 5:1158-61; and Peng et al., Nature Nanotechol. 2009; 4:669-73; the contents of each of these references are hereby incorporated by reference. Synthesized gold nanoparticles were spherical. The nanoparticles were drop-casted onto semi-circular microelectronic transducers, until a resistance of several $M\Omega$ was reached. The devices were dried for 2 hours at ambient temperature and then baked overnight at 50° C. in a vacuum oven. The microelectronic transducers consisted of ten pairs of circular interdigitated (ID) gold electrodes on silicon with 300 nm thermal oxide (Silicon Quest International, Nevada, US). The outer diameter of the circular electrode area was 3 mm, and the gap between two adjacent electrodes and the width of each electrode both 20 m$\Omega$ Gold nanoparticles were molecularly modified with different sensing layers, including, dodecanethiol, octadecanethiol, 1-decanethiol, 3-ethoxythiophenol, 4-chlorobenzene-methanethiol, and hexanethiol. Dodecanethiol, octadecanethiol, 1-decanethiol, 3-ethoxythiophenol, and 4-chlorobenzene-methanethiol were used to prepare gold nanoparticles comprising a monolayer of the capping compounds. Hexanethiol was used to prepare gold nanoparticles comprising from 1 to 6 layers of the capping compound.

The SWCNT sensor was based on an electrically continuous random network of SWCNTs that was formed by drop-casting a solution of SWCNTs (from ARRY International LTD, Germany; ~30% metallic, ~70% semiconducting, average diameter=1.5 nm, length=7 mm) in dimethylformamide (DMF, from Sigma Aldrich Ltd., >98% purity) onto the pre-prepared electrical transducers. After the deposition, the device was slowly dried overnight under ambient conditions to enhance the self-assembly of the SWCNTs and to evaporate the solvent. The procedure was repeated until a resistance of 100 K$\Omega$ to 10 M$\Omega$ was obtained. The microelectronic transducer for the SWCNT sensor consisted of ten pairs of 4.5 mm wide, interdigitated Ti/Pd electrodes on silicon with two microns of thermal oxide (Silicon Quest International, Nevada, US). The SWCNT sensor was organically functionalized with Polycyclic Aromatic Hydrocarbon derivatives, including hexagonal methoxy hexa-perihexabenzocoronene (HBC-1) and semi-triangular methoxy hexa-perihexabenzocoronene (HBC-3). After fabrication, each sensor went through a characterization procedure, in which it was exposed to several concentrations of compounds, usually found in breath, (e.g. isopropyl alcohol, 2-Ethyl-Hexanol, water vapor and others), in range of tens of Parts of billion (ppb)—several Parts per millions (ppm). The information obtained in such experiments allowed choosing the most sensitive, stable and repeatable sensors, to be used for clinical breath samples analysis.

Example 6: Sensors Array Exposure to the Breath Samples and Signal Processing

An exposure stainless steel cell containing 30 different nanomaterial-based chemiresistors were mounted upon a custom polytetrafluoroethene (PTFE) circuit. In order to transfer the VOCs trapped upon the absorption materials, the samples underwent thermal desorption (at 250° C.) in an auto-sampler thermal desorption system (TD20; Shimadzu Corporation, Japan), and the desorbed sample were temporarily stored in a stainless steel VICI® sample loop (Valco Instruments Co. Inc.) at 150° C. In parallel, the chamber containing the sensors was kept under vacuum conditions (~30 mtorr), until the sample was directed into the chamber, the remaining volume was filled with $N_2$ (99.999%) until reaching atmospheric pressure. A Keithley data logger device (model 2701 DMM) was used to sequentially acquire resistance readings from the sensor array, during 5 minutes in vacuum, prior to exposure (baseline) followed by 5 minutes of breath sample that filled the chamber, followed by another 5 minutes of sensors recovery, starting with chamber vacuum. The whole system was controlled by a custom made Lab View program.

During exposure of the sensors to breath samples or to calibration gas, the interaction between the VOCs and the organic sensing layer results in a change in the sensors resistance. During the 5 minuets exposure, and because the diversity in the sensors organic coatings, 30 different time-dependent changes in electrical resistance of the sensors were recorded. This change recovers to baseline resistance almost immediately with evacuating the sample from the chamber. Using the sensors array approach, time-dependent changes in the electrical resistance of the sensors were monitored before, during and after exposure to each breath sample Particularly, from the response of each sensor to each breath sample, four response-induced parameters were extracted: the normalized change of sensor's resistance at the peak, middle and end of the exposure, and the area under curve of whole measured signal.

In order to supervise the sensors' functionality, during the experiment, and also to overcome sensors' response drift, the sensors were exposed to a fixed calibration gas mixture, containing 11.5 ppm isopropyl alcohol, 2.8 ppm tri-methylbenzene and 0.6 ppm 2-ethylhexanol on a daily bases.

Following said exposure, the raw response signals of the sensors to the breath samples were normalized to their response to the calibration gas, measured on the same day. In addition, a humidity compensation method was used in order to reduce the effect of water vapor found in higher levels in samples collected on Tenax and Carboxen trap tubes, due to the ability to adsorb water vapor.

Sensing features were extracted from only from 21 sensors that were functional and stable throughout the whole period of analysis. Nine sensors were excluded from the analysis because of technical difficulties or dysfunction during the analysis phase.

Control experiments to test the reproducibility of the sensing responses and behavior were carried out over periods ranging from six months to three years. Some day-to-day fluctuations were evident in the calibration experiments but their magnitude (noise) was negligible Example 7: Statistical Analysis Multiple linear regression models were applied to the sensing features to test and correct the associations between the covariates (age, sex, location and smoking status) and the numerical outcome. The regression models were then applied again to the adjusted data to verify the correction. Discriminant factor analysis (DFA) as a pattern recognition algorithm was then applied to the data (sensing features) to test the feasibility of the sensors to discriminate among the study sub-populations (diseases), and cross-validation methods and blind tests were used to validate the results.

Discriminant factor analysis is a supervised linear method that is supplied with the classification information regarding every measurement in the training set. Using a linear combination of the input variables E., DFA finds new orthogonal axes (canonical values), in order to minimize the variance within each given class and maximize the variance between two classes. In order to prevent over fitting of the data, a maximum of 3 sensing features was used to build discriminative model, stressing a ratio of 1:10 of features to samples. 30 samples (or less in cases with limited number of patients, as can be seen in Table 1) were randomly chosen and used in order to obtain a binary classifiers using DFA. Out of each group 7 samples were first excluded for blind validation of the acquired classifier; the remaining samples were used as training set. Each of the samples were then classified accordingly and was determined whether the result turned out to be, True Positive (TP), False Positive (FP), True Negative (TN) or False Negative (FN). The classification accuracy was identified by calculating the sensitivity (TP/TP+FN), specificity (TN/TN+FP), and accuracy (TP+TN/sample size) of the constructed model. Binary classifiers have been established using the output of maximum 2-4 sensors for each specific disease.

Each of the test populations afflicted with a particular disease was analyzed by DFA as compared to the healthy control group. Additionally, the obtained classifiers were tested to differentiate between two different types of diseases. Due to the small size of the Prostate cancer population (11 subjects), this group was not analyzed by binary classification.

Example 8: Results of the Sensor Array Analysis of the Breath Samples 61 response induced parameters were extracted from the 21 sensors that were functional and stable throughout the whole period of analysis. Types of the response induced parameters and the corresponding sensors are summarized in Table 14.

TABLE 14

Sensors and response induced parameters used in this study

| SF # | Sensor # | Sensor nanomaterial | Sensor nanomaterial coating | Response induced parameter | # times used in DFA |
|---|---|---|---|---|---|
| SF01 | 10 | GNP | Octadecanethiol | Area Under Curve | 12 |
| SF02 | 10 | GNP | Octadecanethiol | Normalized Delta R middle | 12 |
| SF03 | 10 | GNP | Octadecanethiol | Normalized Delta R peak | 12 |
| SF04 | 12 | GNP | 1-Decanethiol | Area Under Curve | 12 |
| SF05 | 12 | GNP | 1-Decanethiol | Normalized Delta R middle | 12 |
| SF06 | 12 | GNP | 1-Decanethiol | Normalized Delta R peak | 12 |
| SF07 | 14 | GNP | Octadecanethiol | Area Under Curve | 8 |
| SF08 | 14 | GNP | Octadecanethiol | Normalized Delta R middle | 8 |
| SF09 | 17 | GNP | Dodecanethiol | Area Under Curve | 22 |
| SF10 | 17 | GNP | Dodecanethiol | Normalized Delta R end | 22 |
| SF11 | 17 | GNP | Dodecanethiol | Normalized Delta R middle | 22 |
| SF12 | 17 | GNP | Dodecanethiol | Normalized Delta R peak | 22 |
| SF13 | 19 | GNP | 3-ethoxythiophenol | Area Under Curve | 31 |
| SF14 | 19 | GNP | 3-ethoxythiophenol | Normalized Delta R middle | 31 |
| SF15 | 19 | GNP | 3-ethoxythiophenol | Normalized Delta R peak | 31 |
| SF16 | 20 | GNP | 1-Decanethiol | Area Under Curve | 30 |
| SF17 | 20 | GNP | 1-Decanethiol | Normalized Delta R end | 30 |
| SF18 | 20 | GNP | 1-Decanethiol | Normalized Delta R peak | 30 |
| SF19 | 21 | GNP | Dodecanethiol | Area Under Curve | 17 |
| SF20 | 21 | GNP | Dodecanethiol | Normalized Delta R middle | 17 |
| SF21 | 21 | GNP | Dodecanethiol | Normalized Delta R peak | 17 |
| SF22 | 22 | GNP | Dodecanethiol | Area Under Curve | 16 |
| SF23 | 22 | GNP | Dodecanethiol | Normalized Delta R middle | 16 |
| SF24 | 22 | GNP | Dodecanethiol | Normalized Delta R peak | 16 |
| SF25 | 23 | GNP | Dodecanethiol | Area Under Curve | 12 |
| SF26 | 23 | GNP | Dodecanethiol | Normalized Delta R middle | 12 |
| SF27 | 23 | GNP | Dodecanethiol | Normalized Delta R peak | 12 |
| SF28 | 24 | GNP | Dodecanethiol | Area Under Curve | 22 |
| SF29 | 24 | GNP | Dodecanethiol | Normalized Delta R end | 22 |
| SF30 | 24 | GNP | Dodecanethiol | Normalized Delta R middle | 22 |
| SF31 | 24 | GNP | Dodecanethiol | Normalized Delta R peak | 22 |
| SF32 | 25 | GNP | Dodecanethiol | Area Under Curve | 15 |
| SF33 | 25 | GNP | Dodecanethiol | Normalized Delta R middle | 15 |
| SF34 | 25 | GNP | Dodecanethiol | Normalized Delta R peak | 15 |
| SF35 | 26 | GNP | Dodecanethiol | Area Under Curve | 13 |
| SF36 | 26 | GNP | Dodecanethiol | Normalized Delta R end | 13 |
| SF37 | 26 | GNP | Dodecanethiol | Normalized Delta R middle | 13 |
| SF38 | 26 | GNP | Dodecanethiol | Normalized Delta R peak | 13 |
| SF39 | 27 | GNP | Hexanethiol | Area Under Curve | 16 |
| SF40 | 27 | GNP | Hexanethiol | Normalized Delta R middle | 16 |
| SF41 | 27 | GNP | Hexanethiol | Normalized Delta R peak | 16 |
| SF42 | 29 | GNP | 4-chlorobenzene methanethiol | Area Under Curve | 21 |
| SF43 | 29 | GNP | 4-chlorobenzene methanethiol | Normalized Delta R middle | 21 |

TABLE 14-continued

Sensors and response induced parameters used in this study

| SF # | Sensor # | Sensor nanomaterial | Sensor nanomaterial coating | Response induced parameter | # times used in DFA |
|---|---|---|---|---|---|
| SF44 | 29 | GNP | 4-chlorobenzene methanethiol | Normalized Delta R peak | 21 |
| SF45 | 31 | GNP | 1-Decanethiol | Area Under Curve | 8 |
| SF46 | 31 | GNP | 1-Decanethiol | Normalized Delta R middle | 8 |
| SF47 | 31 | GNP | 1-Decanethiol | Normalized Delta R peak | 8 |
| SF48 | 32 | GNP | 1-Decanethiol | Area Under Curve | 10 |
| SF49 | 32 | GNP | 1-Decanethiol | Normalized Delta R middle | 10 |
| SF50 | 32 | GNP | 1-Decanethiol | Normalized Delta R peak | 10 |
| SF51 | 33 | GNP | 1-Decanethiol | Normalized Delta R middle | 4 |
| SF52 | 33 | GNP | 1-Decanethiol | Normalized Delta R peak | 4 |
| SF53 | 34 | SWCNT | HBC-1 | Area Under Curve | 9 |
| SF54 | 34 | SWCNT | HBC-1 | Normalized Delta R middle | 9 |
| SF55 | 34 | SWCNT | HBC-1 | Normalized Delta R peak | 9 |
| SF56 | 36 | SWCNT | HBC-3 | Normalized Delta R middle | 12 |
| SF57 | 9 | GNP | Dodecanethiol | Area Under Curve | 10 |
| SF58 | 9 | GNP | Dodecanethiol | Normalized Delta R end | 10 |
| SF59 | 9 | GNP | Dodecanethiol | Normalized Delta R peak | 10 |

Prior to statistical analysis of the sensing responses, multiple linear regression models were obtained to explore and stratify the effects of possible confounding factors: sex, age, smoking status and location of sampling site. The analysis revealed that of the 59 eligible sensing features, 39 were correlated with age and/or smoking, most of these correlations being negative (i.e. lower signals were obtained from older smokers), while only three of the 59 were correlated with gender, yet none with geographical location. The data were stratified using the linear correlations and second regression models were obtained to ensure the correction was effective.

Figure 3:
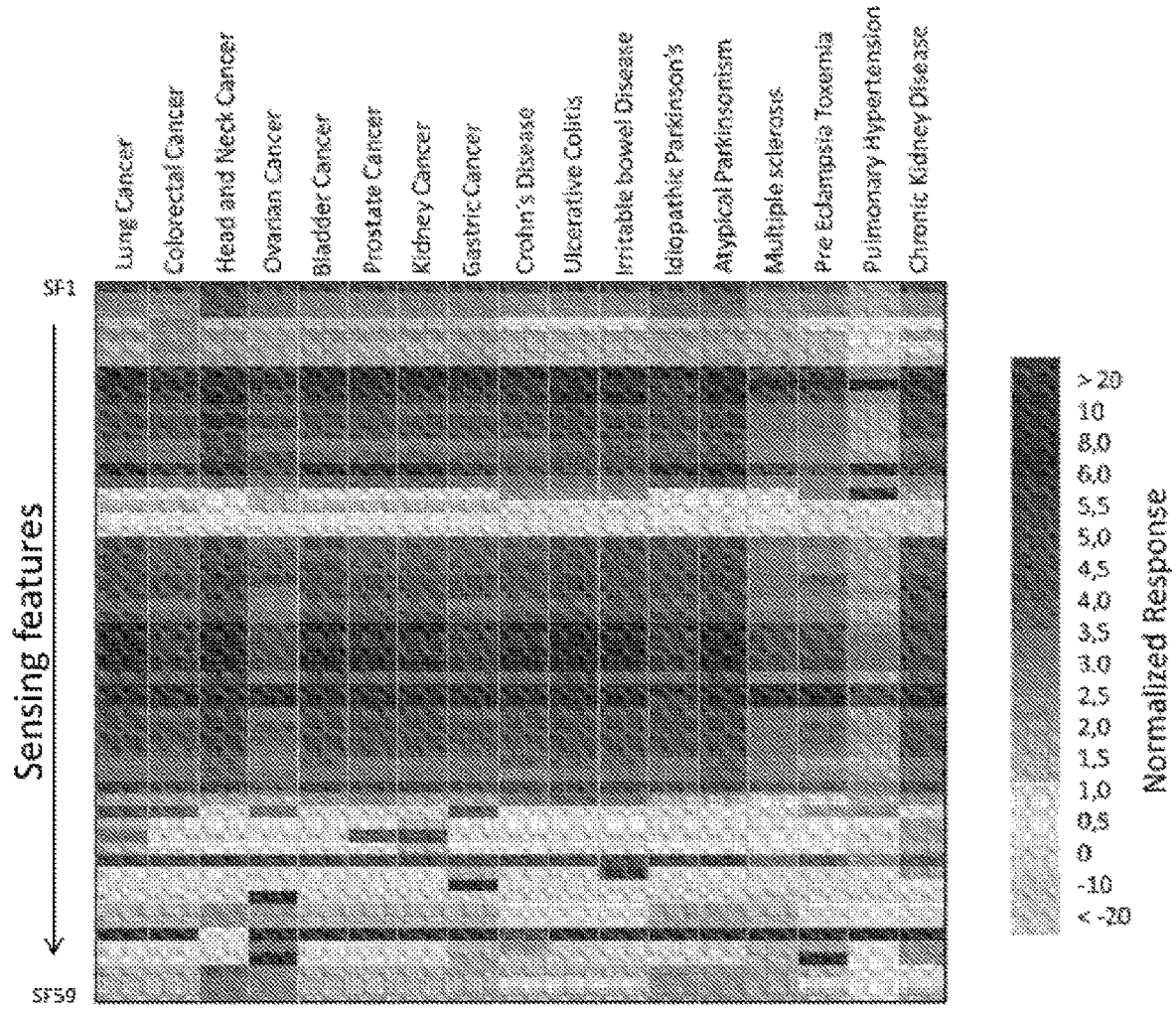
FIG. 3: Heat map (in black and white) of the sensor array responses, including 59 stable response-induced parameters, also termed sensing features, extracted from 20 different nanomaterial-based sensors. The rows in the heat map represent the successive sensing features, from SF1 (top row) to SF59 (bottom row) wherein "SF" stands for sensing feature. Each row datum represents the mean responses to each of the 17 diseases studied by this approach.

FIG. 3 presents a heat map of the nanoarray sensor set responses upon exposure to breath samples from various categories of patients. The figure shows that on exposure to the breath samples, some sensors were unresponsive to the differences between the VOC patterns of the different disease populations, such as SF-29 (FIG. 3, upper arrow). Others were much more sensitive and indicated distinct responses to the breath samples from different diseases, such as SF-43 and SF-44 (FIG. 3, lower arrow). However, none of the individual sensing features was sufficiently informative to discriminate among all the diseases; rather, the overall response patterns showed discriminative potential (columns in FIG. 3). Therefore the more sensitive sensing features were used to create a series of Discriminant Factor Analysis binary classifiers to obtain disease breath signatures that would allow the different diseases to be discriminated. In this analysis, 30 breath samples (fewer for smaller groups) were used, randomly chosen from each group (total of 60 for each model). Forty-six samples were used for the training phase for the classifiers, while the remaining set of 14 independent samples was subsequently used for blind validation.

Figure 4:
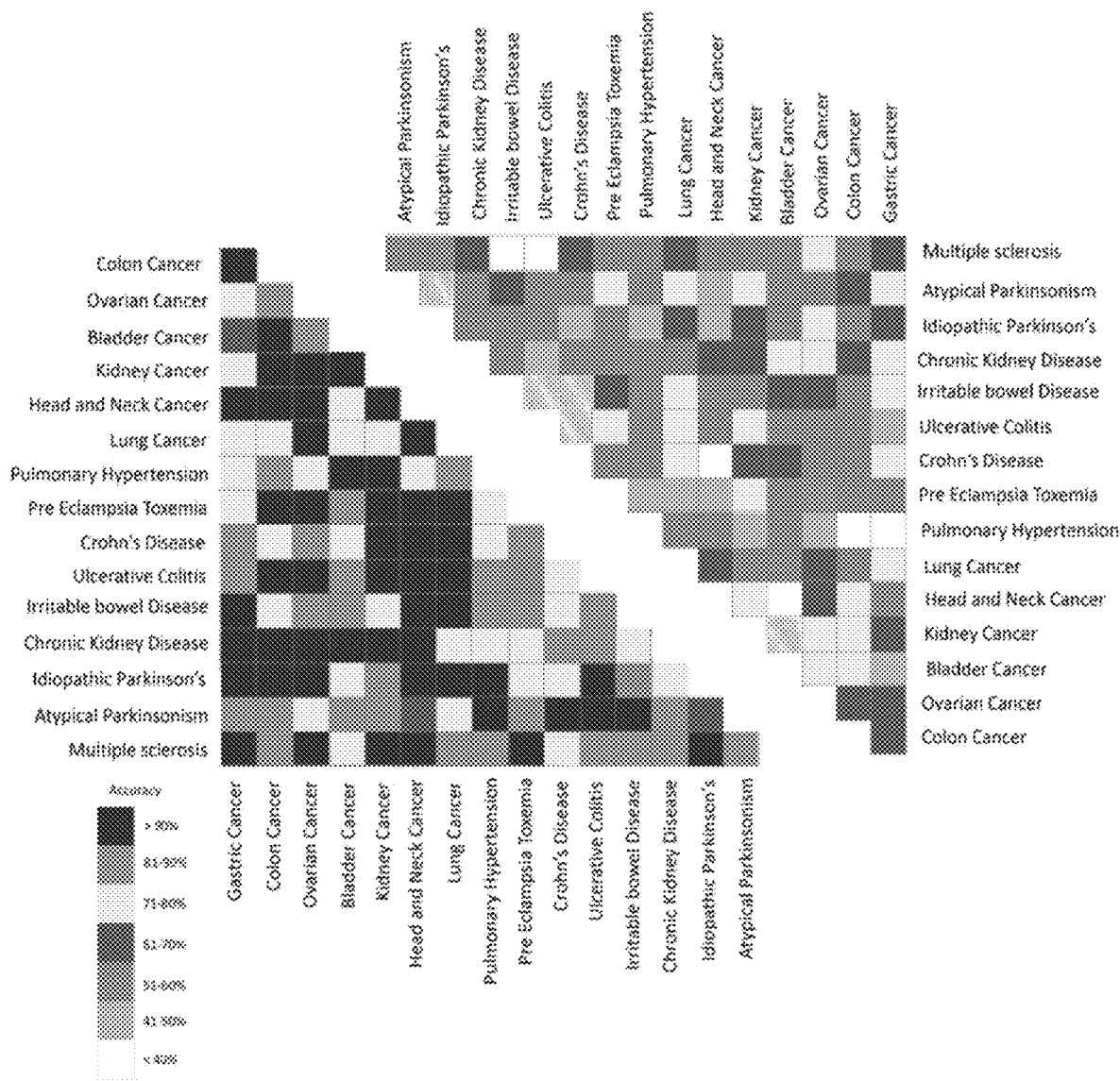
FIG. 4: Graphical presentation of accuracy of binary classifiers used in the sensor array analysis. Each box represents the accuracy achieved in a blind validation of each pair of subject groups. The left heat map represents the results of comparisons between groups of patients, while the heat map on the left represents the results of the same classifiers applied to the corresponding control groups. The average accuracy of all disease classifiers was 86%, while an accuracy of 58% was obtained when the same models were applied to the corresponding control groups.

The analysis consisted of 136 binary models, each discriminating a pair of the studied diseases. The accuracy of the blind analysis of each model was calculated as the total number of samples correctly classified over the total number of independent set samples (n=14). The average accuracy of all 136 classifiers was 86%. While in one case the nanoarray sensor set analysis failed to discriminate between two groups (pre-eclampsia and ulcerative colitis) (accuracy 50%), a maximal accuracy of 100% was found in 10 different comparisons (FIG. 3). To test whether the discrimination achieved between the different groups was influenced by any bias, possibly caused by the confounding factors geography and/or methodology, the classifiers that successfully discriminated among the diseases were applied to the corresponding control groups, collected at the same sites under the same conditions. Once again, 30 randomly-chosen samples were used as a training set and the 14 independent samples for each classifier were classified in a blind manner. This last analysis resulted in accuracies between 28% for PAH vs. CC and 85% for TOX vs. OC, yielding an overall average accuracy for this analysis of 58%. In some cases, two or more diseases shared the same control group, as in Crohn's disease, Ulcerative colitis and Irritable bowel syndrome; Kidney and Bladder cancer; Idiopathic and atypical Parkinsonism; so the last analysis was not applicable to those groups (FIG. 4—boxes with slashes). In contrast to the high accuracy achieved among diseases (86%), the classification of the control samples resulted in random results with a total accuracy of 58%, ruling out the possibility of coincidence. In certain comparisons the results were higher than the arbitrary classification of the control subjects, but the overall results indicated that the sensor analysis is not affected by the bias observed in the quantitative analysis. This is not surprising, since the sensors are cross-reactive and sense the mixture collectively, so the effect of a slight variation in concentration of one or a few VOCs (out of about 80 VOCs on average in a single breath sample) is negligible in most cases. These results show that the nanoarray sensor set could discriminate between 16 different diseases with high accuracy, moreover, the same analysis failed to discriminate between the corresponding groups. These findings stress that the differences in the volatolome, during disease are much more stressed and significant than the minor intra-individual differences were found among control groups.

Three most commonly used sensors in this study were S17—Dodecanethiol capped gold-nanoparticles, S19—3-ethoxythiophenol capped gold-nanoparticles and S-20 1-Decanethiol capped gold-nanoparticles. Said sensors were found to be most sensible to the volatolome differences.

Example 9: Clustering Analysis

Figure 5:
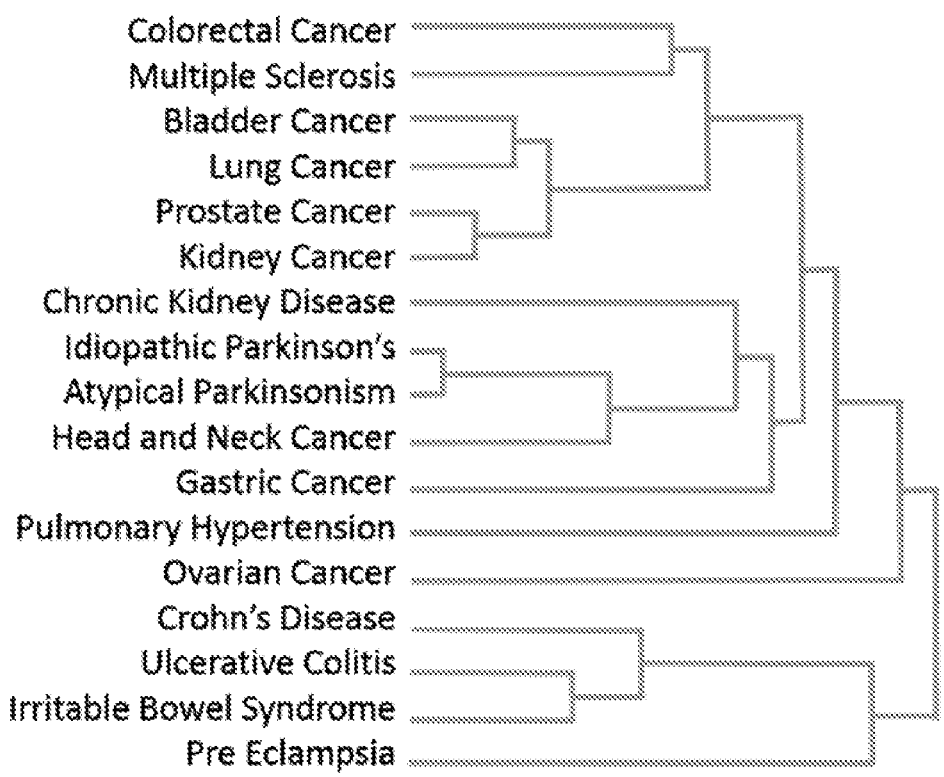
FIG. 5: Clustering analysis for the responses obtained from the sensors, wherein each cluster represents a similar response profile, suggesting considerable resemblance among samples (subjects) in a specific cluster.

To explore similarities and/or differences among the breath volatolomes associated with each disease, a clustering analysis was performed in which the responses of the sensors were clustered and regrouped according to similarities and/or differences in the collective pattern of the volatolome. Each clustering step represents greater similarities between the profiles, suggesting considerable resemblance among the samples (subjects) of a specific cluster. There are two important inferences from the results. The first is that the data were not clustered according to possible confounding factors, such as sampling location, racial and/or ethnic factors, sex or age. For example, no resemblance was found between pre-eclampsia and ovarian cancer, two groups including only female volunteers, moreover, the resemblance between multiple sclerosis and Parkinson disease was negligible, although these samples were obtained from the same exact department. Second, the analysis revealed a strong resemblance among subgroups with common pathophysiologies. For instance, there was high similarity among most of the cancerous diseases, as well as among diseases associated with increased inflammatory activity (CD, UC and pre-eclampsia), while Parkinsonian-related groups (idiopathic and atypical Parkinsonism) were sub-grouped together (FIG. 5).

There were excellent correlations between the nanoarray results and quantitative analysis by GC-MS, which showed that the VOC profiles of cancers had much more in common than non-cancerous diseases. These results support the hypothesis that similarities in pathophysiological processes are expressed in rather similar breath patterns.

Example 10: Universal Diagnosis System Study

The present study is aimed to evaluate the sensitivity, specificity and accuracy of the diagnosing system, which includes three nanosensors including dodecanethiol-capped GNPs, 3-ethoxythiophenol capped GNPs and 1-dodecanethiol capped GNPs and a pattern recognition analyzer, which is configured to compare the output signals of the sensors with the disease specific patterns derived from the database obtained in the experiments described in Examples 6-8.

The test population includes 100 volunteers. One sample is obtained from each volunteer. Out of the 100 volunteers, 70 are previously diagnosed with one of the following diseases: lung cancer, ovarian cancer, colon cancer, kidney cancer, head and neck cancer, bladder cancer, prostate cancer, gastric cancer, ovarian cancer, chronic kidney failure, Crohn's disease, ulcerative colitis, irritable bowel syndrome, pulmonary artery hypertension, pre-eclampsia toxemia, idiopathic Parkinson's, atypical Parkinsonism, and Multiple Sclerosis. The remaining 30 volunteers are healthy subjects that have no evidence for any of the diseases listed hereinabove.

The breath samples are blindly validated. Sensors are exposed to the randomly selected breath samples, time-dependent changes in the electrical resistance of the sensors is monitored and response-induced parameters are extracted from each response as described in Example 6. The response signals obtained from each sample are analyzed by the pattern recognition analyzer based on a DFA algorithm to obtain the closest match between the test signal and the database-derived disease-specific pattern.

The results of diagnosis of each subject performed by the universal diagnosis system are compared with the previously-known diagnosis of said subjects. Diagnosis sensitivity, specificity and accuracy are calculated as follows: A) by combining "other disease" and "healthy" as a control group; B) by two separate comparisons: Diseases A vs Disease B and Disease A vs healthy control.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A system for diagnosing, screening or monitoring a disease in a test subject, the system comprising:
    (a) a selected definitive sensor set comprising at least three sensors reactive to the presence of volatile organic compounds (VOCs) in an exhaled breath of the test subject, the sensors comprising nanomaterials selected from metal nanoparticles coated with a first organic coating and single walled carbon nanotubes (SWCNTs) coated with a second organic coating, wherein the sensor set comprises Au nanoparticles coated with dodecanethiol, Au nanoparticles coated with 1-decanethiol, Au nanoparticles coated with 3-ethoxythiophenol, Au nanoparticles coated with octadecanethiol, Au nanoparticles coated with 4-chlorobenzene methanethiol, Au nanoparticles coated with hexanethiol, and SWCNTs coated with methoxy hexa-perihexabenzocoronene; and
    (b) a processing unit comprising a pattern recognition analyzer, wherein the pattern recognition analyzer is configured to:
    receive output signals of the sensor set;
    compare the output signals to disease-specific patterns derived from a database of response patterns of the sensor set to exhaled breath of subjects with known diseases, wherein each of the disease-specific patterns is characteristic of a particular disease, selected from the group consisting of neurodegenerative diseases, proliferative diseases, renal diseases, respiratory diseases, inflammatory bowel diseases, and obstetric diseases; and
    select a closest match between the output signals of the sensor set and the disease-specific patterns.

2. The system according to claim 1, wherein the selected definitive sensor set provides differentiation between two diseases, selected from the group consisting of Multiple Sclerosis, Alzheimer's disease, Parkinson's disease, lung cancer, colon cancer, head and neck cancer, ovarian cancer, bladder cancer, prostate cancer, kidney cancer, gastric cancer, Crohn's disease, ulcerative colitis, irritable bowel syndrome, pulmonary artery hypertension, chronic kidney disease and pre-eclampsia with an accuracy of at least about 80%.

3. The system according to claim 1, wherein the selected definitive sensor set further comprises metal nanoparticles selected from the group consisting of Au, Ag, Ni, Co, Pt, Pd, Cu, and Al nanoparticles, wherein the metal nanoparticles are coated with compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof.

4. The system according to claim 1, wherein the selected definitive sensor set further comprises SWCNTs coated with compounds selected from the group consisting of propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$), dioctyl phthalate ($C_{24}H_{38}O_4$), 1,2,5,6,9,10-hexabromo-cyclododecane ($C_{12}H_{18}Br_6$), pentadecane ($C_{15}H_{32}$), and combinations thereof.

5. The system according to claim 1, wherein the at least three sensors are configured in a form selected from the group consisting of a capacitive sensor, a resistive sensor, an impedance sensor, and a field effect transistor sensor.

6. The system according to claim 1, further comprising a device which measures the output signals of the sensor set upon exposure to a breath sample, wherein the device measures changes in at least one property of the sensor set, selected from the group consisting of resistance, conductance, alternating current (AC), frequency, capacitance, impedance, inductance, mobility, electrical potential, optical property and voltage threshold.

7. The system according to claim 1, wherein the database comprises response patterns of the sensor set to exhaled breath of at least 500 subjects suffering from a known disease, of which at least 15% are diagnosed with a neurodegenerative disease, at least 30% are diagnosed with a proliferative disease, at least 5% are diagnosed with a renal disease, at least 1% are diagnosed with a respiratory disease, and at least 5% are diagnosed with an inflammatory bowel disease, wherein the neurodegenerative disease is selected from the group consisting of Multiple Sclerosis, Alzheimer's disease, and Parkinson's disease; the proliferative disease is selected from the group consisting of lung cancer, colon cancer, head and neck cancer, ovarian cancer, bladder cancer, prostate cancer, kidney cancer, and gastric cancer; the inflammatory bowel disease is selected from the group consisting of Crohn's disease, ulcerative colitis and irritable bowel syndrome; the respiratory disease comprises pulmonary artery hypertension; and the renal disease comprises chronic kidney disease.

8. A method of diagnosing, screening or monitoring a disease in a test subject, the method comprising the steps of:
(a) providing a system according to claim 1;
(b) exposing the sensor set to an exhaled breath sample of the test subject;
(c) measuring the output signals of the sensor set upon exposure to the breath sample;
(d) comparing the output signals using the pattern recognition analyzer to the database-derived disease-specific patterns; and
(e) selecting the closest match between the output signals of the sensor set and the database-derived disease-specific patterns.

9. The method according to claim 8, wherein step (c) is performed by a device which measures changes in at least one property of the sensor set, selected from the group consisting of resistance, conductance, alternating current (AC), frequency, capacitance, impedance, inductance, mobility, electrical potential, optical property and voltage threshold and/or wherein step (e) is performed by using at least one algorithm selected from the group consisting of artificial neural network (ANN) algorithm, support vector machine (SVM), principal component analysis (PCA), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

10. The method according to claim 8, wherein the sensor set detects at least 10 VOCs selected from the group consisting of 2-ethylhexanol, 3-methylhexane, 5-ethyl-3-methyl-octane, acetone, ethanol, ethyl acetate, ethylbenzene, isononane, isoprene, nonanal, styrene, toluene and undecane.

11. A system for diagnosing, screening or monitoring a disease in a test subject, the system comprising:
(a) a selected definitive sensor set comprising at least three sensors reactive to the presence of volatile organic compounds (VOCs) in an exhaled breath of the test subject, the sensors comprising nanomaterials selected from metal nanoparticles coated with a first organic coating and single walled carbon nanotubes (SWCNTs) coated with a second organic coating, wherein the sensor set comprises Au nanoparticles coated with dodecanethiol, Au nanoparticles coated with 1-decanethiol and Au nanoparticles coated with 3-ethoxythiophenol; and
(b) a processing unit comprising a pattern recognition analyzer, wherein the pattern recognition analyzer is configured to:
receive output signals of the sensor set;
compare the output signals to disease-specific patterns derived from a database of response patterns of the sensor set to exhaled breath of subjects with known diseases, wherein each of the disease-specific patterns is characteristic of a particular disease, selected from the group consisting of neurodegenerative diseases, proliferative diseases, renal diseases, respiratory diseases, inflammatory bowel diseases, and obstetric diseases, and wherein the database comprises response patterns of the sensor set to exhaled breath of at least 500 subjects suffering from a known disease, of which at least 15% are diagnosed with a neurodegenerative disease, at least 30% are diagnosed with a proliferative disease, at least 5% are diagnosed with a renal disease, at least 1% are diagnosed with a respiratory disease, and at least 5% are diagnosed with an inflammatory bowel disease; and
select a closest match between the output signals of the sensor set and the disease-specific patterns.

12. The system according to claim 11, wherein the selected definitive sensor set further comprises metal nanoparticles selected from the group consisting of Au, Ag, Ni, Co, Pt, Pd, Cu, and Al nanoparticles; wherein the metal nanoparticles are coated with compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof.

13. The system according to claim 11, wherein the selected definitive sensor set further comprises SWCNTs coated with compounds selected from the group consisting of propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitromethane ($C_4H_9NO_5$), tetracosane ($C_{24}H_{50}$), dioctyl phthalate ($C_{24}H_{38}O_4$), 1,2,5,6,9,10-hexabromo-cyclododecane ($C_{12}H_{18}Br_6$), pentadecane ($C_{15}H_{32}$), and combinations thereof; or with hexa-perihexabenzocoronene (HBC) molecules which are unsubstituted or substituted by any one of methyl ether (HBC—$OC_1$), 2-ethyl-hexyl (HBC—$C_{6,2}$), 2-hexyldecane (HBC—$C_{10,6}$), 2-decyl tetradecane (HBC—$C_{14,10}$), and dodecane (HBC—$C_{12}$).

14. The system according to claim 11, wherein the sensor set further comprises Au nanoparticles coated with octadecanethiol, Au nanoparticles coated with 4-chlorobenzene methanethiol and Au nanoparticles coated with hexanethiol.

15. The system according to claim 14, wherein the sensor set further comprises SWCNTs coated with methoxy hexa-perihexabenzocoronene.

16. The system according to claim 11, wherein the at least three sensors are configured in a form selected from the group consisting of a capacitive sensor, a resistive sensor, an impedance sensor, and a field effect transistor sensor.

17. The system according to claim 11, wherein the neurodegenerative disease is selected from the group consisting of Multiple Sclerosis, Alzheimer's disease, and Parkinson's disease; the proliferative disease is selected from the group consisting of lung cancer, colon cancer, head and neck cancer, ovarian cancer, bladder cancer, prostate cancer, kidney cancer, and gastric cancer; the inflammatory bowel disease is selected from the group consisting of Crohn's disease, ulcerative colitis and irritable bowel syndrome; the respiratory disease comprises pulmonary artery hypertension; and the renal disease comprises chronic kidney disease.

18. The system according to claim 11, wherein the database further comprises response patterns of the sensor set to exhaled breath of subjects diagnosed with pre-eclampsia.

19. A method of diagnosing, screening or monitoring a disease in a test subject, the method comprising the steps of:
  (a) providing a system according to claim 11;
  (b) exposing the sensor set to an exhaled breath sample of the test subject;
  (c) measuring the output signals of the sensor set upon exposure to the breath sample;
  (d) comparing the output signals using the pattern recognition analyzer to the database-derived disease-specific patterns; and
  (e) selecting the closest match between the output signals of the sensor set and the database-derived disease-specific patterns.

* * * * *